US008877438B2

(12) United States Patent
Yin

(10) Patent No.: US 8,877,438 B2
(45) Date of Patent: Nov. 4, 2014

(54) SELF-ASSEMBLED POLYNUCLEOTIDE STRUCTURE

(75) Inventor: Peng Yin, Brookline, MA (US)

(73) Assignee: California Institute of Technology, Pasadena, CA (US)

( * ) Notice: Subject to any disclaimer, the term of this patent is extended or adjusted under 35 U.S.C. 154(b) by 317 days.

(21) Appl. No.: 13/186,331

(22) Filed: Jul. 19, 2011

(65) Prior Publication Data

US 2012/0022244 A1    Jan. 26, 2012

Related U.S. Application Data

(60) Provisional application No. 61/366,082, filed on Jul. 20, 2010.

(51) Int. Cl.
| | | |
|---|---|---|
| *C12Q 1/68* | (2006.01) | |
| *C07H 21/00* | (2006.01) | |
| *C07H 21/02* | (2006.01) | |
| *C07H 21/04* | (2006.01) | |
| *B82Y 40/00* | (2011.01) | |
| *B82Y 30/00* | (2011.01) | |

(52) U.S. Cl.
CPC  *B82Y 30/00* (2013.01); *B82Y 40/00* (2013.01)
USPC .......... 435/6.1; 536/22.1; 536/23.1; 536/24.3

(58) Field of Classification Search
USPC .................. 435/6.1; 536/22.1, 23.1, 24.3
See application file for complete search history.

(56) References Cited

U.S. PATENT DOCUMENTS

| | | | |
|---|---|---|---|
| 4,714,680 A | 12/1987 | Civin | |
| 4,897,355 A | 1/1990 | Eppstein et al. | |
| 4,965,204 A | 10/1990 | Civin | |
| 5,057,410 A | 10/1991 | Kawasaki et al. | |
| 5,061,620 A | 10/1991 | Tsukamoto et al. | |
| 5,118,801 A | 6/1992 | Lizardi et al. | |
| 5,270,163 A | 12/1993 | Gold et al. | |
| 5,312,728 A | 5/1994 | Lizardi et al. | |
| 5,424,413 A * | 6/1995 | Hogan et al. ............... 536/24.31 |
| 5,459,127 A | 10/1995 | Felgner et al. | |
| 5,563,256 A | 10/1996 | Chakraborty et al. | |
| 5,579,793 A | 12/1996 | Gajewski et al. | |
| 5,643,741 A | 7/1997 | Tsukamoto et al. | |
| 5,677,136 A | 10/1997 | Simmons et al. | |
| 5,691,145 A | 11/1997 | Pitner et al. | |
| 5,716,827 A | 2/1998 | Tsukamoto et al. | |
| 5,750,397 A | 5/1998 | Tsukamoto et al. | |
| 5,928,913 A | 7/1999 | Efstathiou et al. | |
| 5,989,823 A | 11/1999 | Jayasena et al. | |
| 6,242,246 B1 | 6/2001 | Gold et al. | |
| 6,255,469 B1 * | 7/2001 | Seeman et al. ............. 536/23.1 |
| 6,261,783 B1 | 7/2001 | Jayasena et al. | |
| 6,264,825 B1 | 7/2001 | Blackburn et al. | |
| 6,361,944 B1 | 3/2002 | Mirkin et al. | |
| 6,361,945 B1 | 3/2002 | Becker et al. | |
| 6,485,965 B2 | 11/2002 | Klatzmann et al. | |
| 6,506,559 B1 | 1/2003 | Fire et al. | |
| 6,555,367 B1 | 4/2003 | Spence et al. | |
| 6,899,871 B2 | 5/2005 | Kasahara et al. | |
| 7,033,834 B2 | 4/2006 | Valerio et al. | |
| 7,632,641 B2 | 12/2009 | Dirks et al. | |
| 7,727,721 B2 | 6/2010 | Pierce et al. | |
| 7,960,357 B2 | 6/2011 | Dirks et al. | |
| 8,105,778 B2 | 1/2012 | Dirks et al. | |
| 8,124,751 B2 | 2/2012 | Pierce et al. | |
| 8,241,854 B2 | 8/2012 | Yin et al. | |
| 8,318,921 B2 | 11/2012 | Pierce et al. | |
| 8,497,364 B2 | 7/2013 | Pierce et al. | |
| 2002/0034755 A1 * | 3/2002 | Sparks et al. ............... 435/6 |
| 2002/0051769 A1 | 5/2002 | Zhang | |
| 2002/0172950 A1 | 11/2002 | Kenny et al. | |
| 2003/0092162 A1 | 5/2003 | Shankara et al. | |
| 2003/0129611 A1 | 7/2003 | Bao et al. | |
| 2004/0009510 A1 | 1/2004 | Seiwert et al. | |
| 2004/0043386 A1 | 3/2004 | Pray et al. | |
| 2004/0126773 A1 | 7/2004 | Beske et al. | |
| 2004/0223953 A1 | 11/2004 | Kung et al. | |
| 2005/0089864 A1 | 4/2005 | Li et al. | |
| 2005/0112614 A1 | 5/2005 | Cook | |
| 2005/0239061 A1 | 10/2005 | Marshall et al. | |
| 2005/0260635 A1 | 11/2005 | Dirks et al. | |
| 2006/0035375 A1 | 2/2006 | Head et al. | |
| 2006/0088864 A1 | 4/2006 | Smolke et al. | |
| 2006/0228733 A1 | 10/2006 | Pierce et al. | |

(Continued)

FOREIGN PATENT DOCUMENTS

| | | |
|---|---|---|
| EP | 0 273 085 | 7/1988 |
| EP | 1 479 766 | 11/2004 |

(Continued)

OTHER PUBLICATIONS

Richard Hallick "Introduction to DNA structure" pp. 7 of 7 (Copyright 1995). can be found online at www.blc.arizona.edu/molecular_graphics/dna_structure/dna_tutorial.html.*
U.S. Appl. No. 13/186,331, filed Jul. 19, 2011, Yin et al.
U.S. Appl. No. 13/186,315, filed Jul. 19, 2011, Yin et al.
Aagaard et al., "RNAi Therapeutics: Principles, Prospects and Challenges." *Advanced Drug Delivery Reviews* 59 (2007): 75-86.
Allan et al., "A Concise Total Synthesis of (-)-Quinocarcin via Aryne Annulation." *Journal of American Chemical Society* 130 (2008) 17270-17271.
Amarzguioui et al., "Rational design and in vitro and in vitro delivery of Dicer substrate siRNA,", Nature Protocols, vol. 1, No. 2, pp. 508-517, 2006.
Andronescu et al., "A New Algorithm for RNA Secondary Structure Design", J. Mol. Biol., vol. 336, pp. 607-624, 2004.
Asbury, C.L., "Kinesin: world's tiniest biped", Current Opinion in Cell Biology, vol. 17, pp. 89-97, 2005.

(Continued)

*Primary Examiner* — Ethan C Whisenant
(74) *Attorney, Agent, or Firm* — Knobbe, Martens, Olson & Bear, LLP

(57) ABSTRACT

The present application provides polynucleotide structures such as nucleic acid ribbons and nucleic acid tubes, methods for making the polynucleotide structures, and methods for making two-dimensional or three-dimensional objects comprising the nucleic acid ribbons and nucleic acid tubes.

35 Claims, 9 Drawing Sheets

(56) References Cited

U.S. PATENT DOCUMENTS

| | | | |
|---|---|---|---|
| 2006/0234261 | A1 | 10/2006 | Pierce et al. |
| 2007/0087334 | A1 | 4/2007 | Dirks et al. |
| 2007/0117109 | A1 | 5/2007 | Rothemund |
| 2008/0214488 | A1 | 9/2008 | Pierce et al. |
| 2009/0011956 | A1 | 1/2009 | Yin et al. |
| 2009/0123914 | A1 | 5/2009 | Erikson et al. |
| 2009/0197271 | A1 | 8/2009 | Kotlikoff et al. |
| 2009/0247615 | A1 | 10/2009 | Pierce et al. |
| 2009/0291858 | A1* | 11/2009 | Andersen et al. ............ 506/10 |
| 2009/0311799 | A1 | 12/2009 | Sotzing et al. |
| 2010/0021901 | A1 | 1/2010 | Yin et al. |
| 2010/0021904 | A1 | 1/2010 | Pierce et al. |
| 2010/0035233 | A1 | 2/2010 | Yin et al. |
| 2010/0047926 | A1 | 2/2010 | Dirks et al. |
| 2011/0104676 | A1 | 5/2011 | Pierce et al. |
| 2011/0287557 | A1 | 11/2011 | Zhang et al. |
| 2011/0288148 | A1 | 11/2011 | Pierce et al. |
| 2011/0288832 | A1 | 11/2011 | Pierce et al. |
| 2011/0313030 | A1 | 12/2011 | Dirks et al. |
| 2012/0021410 | A1 | 1/2012 | Yin et al. |
| 2012/0022243 | A1 | 1/2012 | Yin et al. |
| 2012/0190835 | A1 | 7/2012 | Pierce et al. |
| 2012/0251583 | A1 | 10/2012 | Rothemund |

FOREIGN PATENT DOCUMENTS

| | | |
|---|---|---|
| EP | 1 634 890 | 3/2006 |
| EP | 2 155 770 | 5/2008 |
| EP | 2 055 781 | 5/2009 |
| EP | 1 730 161 | 9/2010 |
| EP | 1 931 806 | 10/2011 |
| WO | WO 92/03464 | 3/1992 |
| WO | WO 94/01550 | 1/1994 |
| WO | WO 99/31276 | 6/1999 |
| WO | WO 01/40516 | 6/2001 |
| WO | WO 2005/098049 | 10/2005 |
| WO | WO 2006/048025 | 5/2006 |
| WO | WO 2007/008276 | 1/2007 |
| WO | WO 2007/044727 | 4/2007 |
| WO | WO 2008/106658 | 2/2008 |
| WO | WO 2008/144562 | 5/2008 |
| WO | WO 2011/126996 | 4/2011 |

OTHER PUBLICATIONS

Barish, R.D.; Schulman, R.; Rothemund, P.W.K.; Winfree, E., "An Information-Bearing seed for nucleating algorithmic self assembly." Proceedings of the National Academy of Sciences 2009, 106, 6054.

Bates, M.; Huang, B.; Dempsey, G.T.; and Zhuang, X. "Multicolor super-resolution imaging with photo-switchable fluorescent probes." Science, 317: 1749-1759, 2007.

Behenna et al., "The Enantioselective Tsuji Allylation." Journal of American Chemical Society 126.46 (2004): 15044-15045.

Bloomfield et al., "Nucleic Acids: Structures, Properties, and Functions." University Science Books (2000).

Bois et al., "Topological constraints in nucleic acid hybridization kinetics", Nucleic Acids Research, vol. 33, No. 13, pp. 4090-4095, 2005.

Bolt et al., Differential Reactivities of the mono- and di-epoxide of 1,3-butadiene. Toxicology 113 (1996): 294-296.

Bumcrot et al., "RNAi Therapeutics: A Potential New Class of Pharmaceutical Drugs." Nature Chemical Biology 2.12 (Dec. 2006): 711-719.

Bushnell et al., "ProbeDesigner: for the design of probesets for branched DNA (bDNA) signal amplification assays," Bioinformatics, 15(5), pp. 348-355, 1999.

Butterfoss et al., Computer-Based Design of Novel Protein Structures, Annu. Rev. Biophys. Biomol. Struct., vol. 35, pp. 49-65, 2006.

Caltech News Release, "Caltech Scientists Create New Process to Program", Sep. 6, 2010.

Caplen, "RNAi as a gene therapy approach", Expert Opin. Biol. Ther., vol. 3, No. 4, pp. 575-586, 2003.

Castanotto et al., "The Promises and Piffalls of RNA-Interlace-Based Therapeutics." Nature 457 (Jan. 22, 2009):426-433.

Cerutti et al., "On the Origin and Functions of RNA-Mediated Silencing: From Protists to Man." Current Genetics 50 (2006) 81-99.

Check, "RNA to the rescue?", Nature, vol. 425, pp. 10-12, Sep. 4, 2003.

Chen, H.L.; Cheng, Q.; Goel, A.; Huang, M.D. Espanes, P.M.d. "Invadable self-assembly: Combining robustness with efficiency." In Proceedings of the 15$^{th}$ annual ACM-SIAM Symposium on Discrete Algorithms (SODA); 2004.

Chen Y.; Liu, H.P.; Ye, T.; Kim, J.; Mao, C.D. "DNA-Directed Assembly of Single-Wall Carbon Nanotubes." J.Am. Chem. Soc. 2007,129.

Coburn et al., "siRNAs: a new wave of RNA-based therapeutics", Journal of Antimicrobial Chemotherapy, vol. 51, pp. 753-756, 2003.

Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.

Coleman et al., "Template-Directed Corss-Linking of Oligonucleotides: Site-Specific Covalent Modification of dG-N7 Within Duplex DNA." J. Org. Chem. 60 (1995): 6252-6253.

Collins et al., "A branched DNA signal amplification assay for quantification of nucleic acid targets below 100 molecules/ml," Nucleic Acids Res, 25(15), pp. 2979-2984, 1997.

Coppelli et al., "Oligonucleotides as Anticancer Agents: From the Benchside to the Clinic and Beyond", Current Pharmaceutical Design, vol. 11, pp. 2825-2840, 2005.

Cullen et al., "Genome-wide Screening for Gene Function Using RNAi in Mammalian Cells." Immunology and Cell Biology 83 (2005) 217-223.

Czauderna et al., "Structural Variations and Stabilising Modifications of Synthetic siRNAs in Mammalian Cells." Nucleic Acids Research 31.11 (2003): 2705-2716.

Definition for "substantial" from Merriam-Webster Online Dictionary. Downloaded from merriam-webster.com; downloaded on Mar. 5, 2008.

Dias et al., "Antisense Oligonucleotides: Basic Concepts and Mechanisms." Molecular Cancer Therapeutics 1 (Mar. 2002) 347-355.

Dietz, H.; Douglas, S.; Shih, W. "Folding DNA into Twisted and Curved Nanoscale Shapes." Science 2009, 325, 725-730.

Dirks et al., "An Algorithm for Computing Nucleic Acid Base-Pairing Probabilities Including Pseudoknots." Journal of Computational Chemistry 25.10 (2004): 1295-1304.

Dirks et al., "A Partition Function Algorithm for Nucleic Acid Secondary Structure Including Pseudoknots." Journal of Computational Chemistry 24.13 (2003) 1664-1677.

Dirks et al., "Paradigms for computational nucleic acid design," Nucleic Acids Research, vol. 32, No. 4, pp. 1392-1403, Oxford University Press, 2004.

Dirks et al., "Thermodynamic Analysis of Interacting Nucleic Acid Strands." SIAM Review 49.1 (2007): 65-88.

Dirks et al., "Triggered amplification by hybridization chain reaction," PNAS, vol. 101, No. 43, pp. 15275-15278, Oct. 26, 2004.

Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.

Douglas et al., "DNA-nanotube-induced alignment of membrane proteins for NMR structure determination", PNAS, vol. 104, No. 16, pp. 6644-6648, Apr. 17, 2007.

Douglas et al., "Self-assembly of DNA into nanoscale three-dimensional shapes", Nature, vol. 459, pp. 414-418, May 21, 2009.

Eckstein, F. "Phosphrothioate oligodeooxynucleotides: what is their origin and what is unique about them?" Antisense Nucleic Acid Drug Dev., 10:117-121, 2000.

Eddy, S.R. "Non-coding RNA genes and the modern RNA world." Nature Reviews, 2: 919-929, 2001.

Elbashir et al., "Functional anatomy of siRNAs for mediating efficient RNAi in Drosophila melanogaster embryo lysate", The EMBO Journal, vol. 20, No. 23, pp. 6877-6888, 2001.

Elghanian et al.,"Selective colorimetric detection of polynucleotides based on the distance-dependent optical properties of gold nanoparticles," Science, 277(5329), pp. 1078-1081, 1997.

(56) References Cited

OTHER PUBLICATIONS

Ellington et al., "In vitro selection of RNA molecules that bind specific ligands," Nature 346, pp. 818-822, 1990.

Elmén et al., "Locked Nucleic Acid (LNA) Mediated Improvements in siRNA Stability and Functionality." *Nucleic Acids Research* 33.1 (2005): 439-447.

Enquist et al.., "The Total Synthesis of (−)-Cyanthiwigin F by Means of Double Catalytic Enantioselective Alkylation." *Nature* 453.7199 (Jun. 26, 2008) 1228-1231.

Extended European Search Report dated Apr. 22, 2010 in European Patent Application No. 06836249.0.

Extended European Search Report from Application No. 08755764. 1, dated Nov. 7, 2011.

Feldkamp et al., "Rational Design of DNA Nanoarchitectures", Angew. Chem. Int. Ed., vol. 45, pp. 1856-1876, 2006.

Felgner, et al., "Nomenclature for Synthetic Gene Delivery Systems", Human Gene Therapy, vol. 8, pp. 511-512, Mar. 20, 1997.

Femino et al., "Visualization of Single Molecules of mRNA in Situ." *Methods of Enzymology* 361 (2003): 245-304.

Ferkol et al., "Gene Transfer into the Airway Epithelium of Animals by Targeting the Polymeric Immunoglobulin Receptor", J. Clin. Invest., vol. 95, pp. 493-502, Feb. 1995.

Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.

Ferreira et al., "The Palladium-Catalyzed Oxidative Kinetic Resolution of Secondary Alcohols with Molecular Oxygen." *Journal of American Chemical Society* 123.31 (2001): 7725-7726.

File history of U.S. Appl. No. 13/186,228.

File history of U.S. Appl. No. 13/186,315.

Final Office Action dated May 27, 2010 for U.S. Appl. No. 11/544,306.

Final Office Action dated Sep. 20, 2010 for U.S. Appl. No. 12/454,799.

Final Office Action dated Sep. 17, 2010 for U.S. Appl. No. 12/467,755.

Final Office Action dated Oct. 15, 2010 for U.S. Appl. No. 12/152,893.

Final Office Action dated Jul. 15, 2011 for U.S. Appl. No. 12/040,735.

Final Office Action dated Jul. 25, 2011 for U.S. Appl. No. 12/395,489.

Fire et al., "Potent and specific genetic interference by double-stranded RNA in *Caenorhabditis elegans*", Nature, vol. 391, pp. 806-811, Feb. 19, 1998.

Flamm et al., "RNA folding at elementary step resolution," RNA, vol. 6, pp. 325-338, 2000.

Friedrich et al., A Cellular Screening Assay to Test the Ability of PKR to Induce Cell Death in Mammalian Cells, Molecular Therapy, vol. 12, No. 5, pp. 969-975, Nov. 2005.

Friedrich et al., "RNA molecules as anti-cancer agents", Seminars in Cancer Biology, vol. 14, pp. 223-230, 2004.

Fu et al., "DNA Double-Crossover Molecules", Biochemistry, vol. 32, pp. 3211-3220, 1993.

Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.

Garg et al., "Development of an Enantiodivergent Strategy for the Total Synthesis of (+)- and (−)-Dragmacidin F from a Single Enantiomer of Quinic Acid." *Journal of American Chemical Society* 127 (2005) 5970-5978.

Garg et al., "A Ligand-free Solid-supported System for Sonogashira Couplings: Applications in Nucleoside Chemistry." *Chem. Commun.* (2005) 4551-4553.

Gilman et al., "The Biological Actions and Therapeutic Applications of the B-Chloroethyl Amines and Sulfides." *Science* 103.2675 (Apr. 5, 1946): 409-415.

Goodman, R.P.; Schaap, I.A.T.; Tardin, C.F.; Erben, C.M.; Berry, R.M.; Schmidt, C.F.; and Turberfield, A.K. "Rapid chiral assembly of rigid DNA blocks for molecular nanofabrication." Science, 310, 2005.

Green et al., "DNA Hairpins: Fuel for Autonomous DNA Devices", Biophysical Journal, vol. 91, pp. 2966-2975, Oct. 2006.

Hansma et al., "DNA Binding to Mica Correlates with Cationic Radius: Assay by Atomic Force Microscopy", Biophysical Journal, vol. 70, pp. 1933-1939, Apr. 1996.

Hashimoto et al., "Recent Progress in Diazirine-Based Photoaffinity Labeling." *Eur. J. Org. Chem.* (2008): 2513-2523.

Haugland RP. The Handbook: A Guide to Fluorescent Probes and Labeling Technologies. 10th Ed. Molecular Probes/Invitrogen; 2005.

Hearst et al., "Psoralen Photochemistry." *Ann.Rev. Biophys.Bioeng.* 10 (1981): 69-86.

Heidel, J.D., "Targeted, systematic non-viral delivery of small interfering RNA in vivo", Doctoral thesis, California Institute of Technology, pp. 1-128, 2005.

Hello, S.W. "Far-field optical nanoscopy." Science, 316: 1153-1158, 2007.

Herath et al., "Synthesis of Acrimarins from 1,3,5-Trioxygenated-9-acridone Derivatives." *Journal of Heterocyclic Chem.* 41 (2004): 23-28.

Higuchi et al. Selective regulation of mutant K-ras mRNA expression by photo-cross-linking antisense oligonucleotide. Nucleic Acids Symposium Series (2007) vol. 51 (1) pp. 443-444.

Hofacker et al., "Fast folding and comparison of RNA secondary structures," Monatshefte für Chemie, vol. 125, pp. 167-188, 1994.

Hokaiwado et al., "RNAi-based drug discovery and its application to therapeutics", IDrugs, vol. 11, No. 4, pp. 274-278, 2008.

Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." Cancer Research 65.19 (Oct. 1, 2005): 8984-8992.

Hughes et al., "Double Labeling wit Fluorescence in Situ Hybridization in *Drosophila* Whole-Mount Embryos," BioTechniques, 24(4), pp. 530-532, 1998.

Huizenga et al., "A DNA Aptamer That Binds Adenosine and ATP." Biochemistry 34, pp. 656-665, 1995.

International Search Report and Written Opinion from PCT/US2005/009471, dated Mar. 8, 2006.

International Search Report and Written Opinion from PCT/US2008/055559, dated Sep. 3, 2008.

Iqbal et al., "A review of molecular recognition technologies for detection of biological threat agents", Biosensors & Bioelectronics, vol. 15, pp. 549-578, 2000.

Jagus et al., "PKR, apoptosis and cancer", The International Journal of Biochemistry & Cell Biology, vol. 31, pp. 123-138, 1999.

Jhaveri et al., "In vitro selection of signaling aptamers", Nature Biotechnology, vol. 18, pp. 1293-1297, Dec. 2000.

Judge et al., "Design of Noninflammatory Synthetic siRNA Mediating Potent Gene Silencing in Vivo." *Molecular Therapy* 13.3 (Mar. 2006): 494-505.

Judge et al., "Overcoming the Innate Immune Response to Small Interfering RNA", Human Gene Therapy, vol. 19, pp. 111-124, Feb. 2008.

Julian et al., "Biomimetic Approaches to Gas Phase Peptide Chemistry: Combining Selective Binding Motifs with Reactive Carbene Precursors to Form Molecular Mousetraps." *International Journal of Mass Spectrometry* 228 (2003): 851-864.

Julian et al., "Molecular Mousetraps: Gas-Phase Studies of the Covalent Coupling of Noncovalent Complexes Initiated by Reactive Carbenes Formed by Controlled Activation of Diazo Precursors." *Agnew. Chem.Int. Ed.* 42.9 (2003) 1012-1015.

Kadnikov et al., "Synthesis of Coumarins via Palladium-Catalyzed Carbonylative Annulation of Internal Alkynes by o-Iodophenols." *Organic Letters* 2.23 (2000): 3643-3646.

Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.

(56) References Cited

OTHER PUBLICATIONS

Kim et al., "Synthetic dsRNA Dicer substrates enhance RNAi potency and efficacy", Nature Biotechnology, vol. 23, No. 2, pp. 222-226, Feb. 2005.
Kim et al., "Strategies for Silencing Human Disease Using RNA Interference." *Nature Review Genetics* 8 (Mar. 2007) 173-184.
Kislauskis et al. "Isoform-specific 3'-untranslated Sequences Sort α-cardiac and β-cytoplasmic Actin Mesenger RNAs to Different ytoplasmic Compartments," The Journal of Cell Biology, 123(1), pp. 165-172, 1993.
Knorre et al., "Photoaffinity Labeling as an Approach to Study Supramolecular Nucleoprotein Complexes." *FEBS Letters* 433 (1998): 9-14.
Kobertz et al., "An Efficient Synthesis of a Furan-Side Furocoumarin Thymidine Monoadduct." *J. Org. Chem.* 62.8 (1997) 2630-2632.
Kobertz et al., "Solid-Phase Synthesis of Oligonucleotides Containing a Site-Specific Psoralen Derivative." *Journal of American Chemical Society* 119 (1997): 5960-5961.
Kobertz et al., "Total Synthesis of a Cis-Syn 2-Carbomethoxypsoralen Furan-Side Thymidine Monoadduct." *Journal of American Chemical Society* 118 (1996): 7101-7107.
Kosman, et al., "Multiplex Detection of RNA Expression in *Drosophila* Embryos," Science, 305, p. 846, 2004.
Kuzuya et al., "Six-Helix and Eight-Helix DNA Nanotubes Assembled from Half-Tubes", Nano Lett., vol. 7, No. 6, pp. 1757-1763, 2007.
Lacenere et al., "Effects of a Modified Dye-Labeled Nucleotide Spacer Arm on Incorporation by Thermophilic DNA Polymerases." *Nucleosides, Nucleotides, and Nucleic Acids* 25 (2006) 9-15.
Ladiges, et al., "Tissue specific expression of PKR protein kinase in aging B6D2F1 mice," Mechanisms of Ageing and Development, vol. 114, pp. 123-132, (2000).
Lawley et al., "DNA Adducts from Chemotherapeutic Agents." *Mutation Research—Fundamental and Molecular mechanisms of Mutagenesis* 355 (1996): 13-40.
Lawrence et al., "Highly Localized Tracks of Specific Transcripts within Interphase Nuclei Visualized by in Situ Hybridication," Cell, 57, pp. 493-502, 1989.
Layzer et al., "In Vivo Activity of Nuclease-Resistant siRNAs." *RNA* 10 (2004): 766-771.
Le et al., "DNA-Templated Self-Assembly of Metallic Nanocomponent Arrays on a Surface", Nano Lett., vol. 4, No. 12, pp. 2343-2347, 2004.
Lee, J.F., Hesselberth, J.R.; Meyers, L.A.; and Ellington, A.D. "Aptamer database." Nucleic Acids Research, 32: D95-100, 2004.
Lee et al., "A self-replicating peptide", Nature, vol. 382, pp. 525-528, Aug. 8, 1996.
Levsky et al., "Single-Cell Gene Expression Profiling," Science 297, pp. 836-840, 2002.
Levy et al., "Exponential growth by cross-catalytic cleavage of deoxyribozymogens", PNAS, vol. 100, No. 11, pp. 6416-6421, May 27, 2003.
Li, H.; LaBean, T.H.; Kenan, D.J. "Single-chain antibodies against DNA aptamers for use as adapter molecules on DNA tile arrays in nanoscale materials organization." Organic and Biomolecular Chemistry 2006, 3420-3426. 2006.
Li, Z, Trimble, M.J.; Brun, Y.V.; Jensen, G.J. "The structure of FtsZ filaments in vivo suggests a force-generating role in cell division." EMBO J.,26, pp. 4694-4708. 2007.
Lin et al., "DNA Tile Based Self-Assembly: Building Complex Nanoarchitectures", ChemPhysChem, vol. 7, pp. 1641-1647, 2006.
Liu et al., "A colorimetric lead biosensor using DNAzyme-directed assembly of gold nanoparticles," J. Am. Chem. Soc., 125(22), pp. 6642-6643, 2003.
Liu et al., "Approaching the Limit: Can One DNA Oligonucleotide Assemble into Large Nanostructures?", Angew. Chem. Int. Ed., vol. 45, pp. 1942-1945, 2006.
Liu et al., "DNA nanotubes self-assembled from triple-crossover tiles as templates for conductive nanowires", PNAS, vol. 101, No. 3, pp. 717-722, Jan. 20, 2004.

Macechko et al., "Comparison of Immunologic Amplification vs Enzymatic Deposition of Fluorochrome-conjugated Tyramide as Detection Systems for Fish," J Histochem Cytochem, 45(3), pp. 359-363, 1997.
Mahato et al., "Modulation of gene expression by antisense and antigene oligodeoxynucleotides and small interfering RNA", Expert Opin. Drug Deliv., vol. 2, No. 1, pp. 3-28. 2005.
Manche et al., "Interactions between Double-Stranded RNA Regulators and the Protein Kinase DAI", Molecular and Cellular Biology, vol. 12, No. 11, pp. 5238-5248, Nov. 1992.
Manoharan et al., "RNA Interference and Chemically Modified Small Interfering RNAs." *Current Opinion in Chemical Biology* 8 (2004): 570-579.
Mathieu et al., "Six-Helix Bundles Designed from DNA", Nano Lett., vol. 5, No. 4, pp. 661-665, 2005.
Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.
Meinhardt et al., "Wavelength-dependent Penetration Depths of Ultraviolet Radiation in Human Skin." Journal of Biomedical Optics 13.4 (Jul./Aug. 2008) 044030-1-044030-5.
Mitchell et al., "Self-Assembly of Chiral DNA Nanotubes", J. Am. Chem. Soc., vol. 126, pp. 16342-16343, 2004.
Mittelstadt, et al., "Interaction of human tRNA-dihydrouridine synthase-2 with interferon-induced protein kinase PKR," Nucleic Acids Research, vol. 36, No. 3, pp. 998-1008, (2008).
Mohr et al., "Catalytic Enantioselective Decarboxylative Protonation." *Journal of American Chemical Society* 128.35 (2006): 11348-11349.
Mohr et al., "Natural Products as Inspiration for the Development of Asymmetric Catalysis." *Nature* 455 (Sep. 18, 2008) 323-332.
Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292,American Chemical Society, 2002.
Naked Scientists (The): Science Radio & Science Podcasts, "RNA-away cancer cells", Sep. 12, 2010, http://www.thenakedscientists.com/HTML/content/news/news/2051/.
National Science Foundation, "These Cells Will Self-Destruct in Five . . . Four . . . ", Press Release 10-160, p. 1-3.
Noll et al., "Formation and Repair of Interstrand Cross-Links in DNA." *Chemical Reviews* 106.2 (2006) 277-301.
Noll et al., "Preparation of Interstrand Cross-Linked DNA Oligonucleotide Duplexes." *Frontiers in Bioscience* 9 (Jan. 1, 2004): 421-437.
Nutiu et al., "Structure-switching signaling aptamers," J. Am. Chem. Soc., vol. 125, pp. 4771-4778, American Chemical Society, 2003.
Office Action dated Feb. 4, 2010 in U.S. Appl. No. 12/152,893.
Office Action dated Apr. 1, 2010 in U.S. Appl. No. 12/467,755.
Office Action dated Apr. 16, 2010 in U.S. Appl. No. 12/454,799.
Office Action dated Dec. 16, 2010 for U.S. Appl. No. 12/395,489.
Office Action dated Mar. 10, 2011 in U.S. Appl. No. 12/454,743, filed May 22, 2009.
Office Action dated Mar. 17, 2011 for U.S. Appl. No. 12/611,875.
Office Action dated Oct. 14, 2011 for U.S. Appl. No. 12/454,743.
Opalinska et al., "Nucleic-Acid Therapeutics: Basic Principles and Recent Applications", Nature Reviews Drug Discovery, vol. 1, pp. 503-514, 2002.
Park, S.H.; Yin, P.; Liu, Y.; Reif, J.H.; LaBean, T.H.; Yan, H. "Programmable DNA Self-Assemblies for Nanoscale Organization of Ligands and Proteins." Nano Letters 2005, 5, 729-733.
Park et al., "Rapid Identification of *Candida dubliniensis* Using a Species-Specific Molecular Beacon", Journal of Clinical Microbiology, vol. 38, No. 8, pp. 2829-2836, 2000.
Park et al., "Three-Helix Bundle DNA Tiles Self-Assemble into 2D Lattice or 1D Templates for Silver Nanowires", Nano Lett., vol. 5, No. 4, pp. 693-696, 2005.
Paul et al., "A self-replicating ligase ribozyme", PNAS, vol. 99, No. 20, pp. 12733-12740, Oct. 1, 2002.
Perales et al., "Gene Transfer in vivo: Sustained Expression and Regulation of Genes Introduced into the Liver by Receptor-Targeted

(56) References Cited

OTHER PUBLICATIONS

Uptake", Proceedings of the National Academy of Sciences of the United States of America, vol. 91, pp. 4086-4090, Apr. 1994.
Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.
Pistona, D.W., and Gremersa, G.J. "Fluorescent protein FRET: the good, the bad and the ugly." Trends in Biochemical Sciences, 32, 2007.
Player et al., "Single-copy Gene Detection Using Branched DNA (bDNA)) in Situ Hybridization," J. Histochem & Cytochem, 49(5), pp. 603-611, 2001.
Pouton et al., "Key issues in non-viral gene delivery", Advanced Drug Delivery Reviews, vol. 46, pp. 187-203, 2001.
Qi et al., "Surface Transfer Doping of Diamond (100) by Tetrafluoro-tetracyanoquinodimethane", J. Am. Chem. Soc., vol. 129, pp. 8084-8085, 2007.
Qian et al., "Recent Developments in Signal Amplification Methods for in Situ Hybridization," Diagnostic Molecular Pathology, 12(1), pp. 1-13, 2003.
Qian, X., L. Jin, and R.V. Lloyd, In situ hybridization: basic approaches and recent development. The Journal of Histotechnology, 2004. 27(1): p. 53-67.
Rachofsky et al., "Probing structure and dynamics of DNA with 2-aminopurine: Effects of local environment on fluorescence," Biochemistry, vol. 40, pp. 946-956, 2001.
Raj et al., "Imaging Individual mRNA Molecules Using Multiple Singly Labeled Probes." *Nature Methods* 5.10 (Oct. 2008): 877-879.
Read et al., "Barriers to Gene Delivery Using Synthetic Vectors", Advances in Genetics, vol. 53, pp. 19-46, 2005.
Reif, J.H.; Sahu, S.; Yin, P. "Compact Error-Resilient Computational DNA tiling Assemblies." In Proc. $10^{th}$ International Meeting on DNA Computing; 2004.
Reif, J.H.; Sahu, S.; Yin, P. "Complexity of Graph Self-Assembly in Accretive Systems and Self-Destructible Systems." In Proc. $11^{th}$ International Meeting on DNA Computing; 2005.
Reynolds et al., "Rational siRNA Design for RNA Interference." *Nature Biotechnology* 22.3 (Mar. 2004) 326-330.
Rothemund, P.; Papadakis, J.; Winfree, E. "Algorithmic Self-Assembly of DNA Sierpinski Triangles." PLoS Biology 2004, 2, 2041-2053.
Rothemund et al., "Design and Characterization of Programmable DNA Nanotubes", J. Am. Chem. Soc., vol. 126, pp. 16344-16352, 2004.
Rothemund, P.W.K., "Folding DNA to creat nanoscale shapes and patterns", Nature, vol. 440, pp. 297-302, 2006.
Rothemund, P.W.K.; Winfree, E. "The Program-size complexity of self-assembled squares (extended abstract)." In Proceedings of the thirty-second annual ACM symposium on Theory of computing; ACM Press: 2000.
Sahu, S.; Yin, P.; Reif, J.H. "A Self-Assembly Model of Time-Dependent Glue Strength." In Proc. $11^{th}$ International meeting on DNA Computing; 2005.
Saunders et al., "Introduction of DNA into Bacteria." *Methods in Microbiology* 29 (1999): 3-49.
Schärer et al., "DNA Interstrand Crosslinks: Natural and Drug-Induced DNA Adducts that Induce Unique Cellular Responses." *ChemBioChem* 6 (2005): 27-32.
Scherer et al., "Approaches for the sequence-specific knockdown of mRNA", Nature Biotechnology, vol. 21, No. 12, pp. 1457-1465, 2003.
Schipani, Vanessa, "A targeted cancer therapy?" The Scientist, Sep. 7, 2010 blog post, http://www.the-scientist.com/blog/display/57674/.
Schulman et al., "Synthesis of crystals with a programmable kinetic barrier to nucleation", PNAS, vol. 104, No. 39, pp. 15236-15241, Sep. 25, 2007.
Schulte-Merker et al., "no tail (ntl) is the zebrafish homologue of the mouse T (Brachyury) gene." *Development* 120 (1994): 1009-1015.
Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.
Schweitzer et al., "Combining nucleic acid amplification and detection," Curr Opin Biotechnol, 12, pp. 21-27, 2001.
Seelig et al., "Catalyzed Relaxation of a Metastable DNA Fuel", Journal American Chemical Society, vol. 128, No. 37, pp. 12211-12220, 2006.
Seeman, "De Novo Design of Sequences for Nucleic Acid Structural Engineering", Journal of Biomolecular Structure & Dynamics, pp. 573-581, vol. 8, No. 3, 1990.
Seeman, "DNA in a material world", Department of Chemistry, New York University, Nature, vol. 421, pp. 427-431 (Jan. 23, 2003).
Seeman, "Nucleic acid junctions and lattices," J. Theor. Biol., vol. 99, pp. 237-247, Academic Press Inc. (London) Ltd., 1982.
Seeman, "Nucleic acid nanstructures and topology", Angew. Chem. Int. Ed. vol. 37, pp. 3220-3238 (1998).
Sekulic, A.; Hudson, C.C; Homme, J.L.; Yin, P.; Otterness, D.M.; Karnitz, L.M.; Abraham, R.T. A Direct Linkage between the Phosphoinositide 3-Kinase-AKT Signaling Pathway and the Mammalian Target of Rapamycin in Mitogen-stimulated and Transformed Cells. Cancer Research 2000, 60, 3504-3513.
Shah et al., "The Fries Isomerization of Acetyl and Benzoyl Esters of Umbelliferones." *J. Org. Chem.* 19 (1954): 1681-1685.
Sharma, J.; Chhabra, R.; Cheng, a.; Brownell, J.; Liu, Y.; Yan, H. "Control of Self-Assembly of DNA Tubules through Integration of Gold Nanoparticles" Science 2009, 112-116.
Sharma et al., "DNA-Tile-Directed Self-Assembly of Quantum Dots into Two-Dimensional Nanopatterns", Angew. Chem. Int. Ed., vol. 47, pp. 5157-5159, 2008.
Shih et al., "A 1.7-kilobase single-stranded DNA that folds into a nanoscale octahedron", Nature, vol. 427, pp. 618-621, Feb. 12, 2004.
Shir et al., "Inhibition of glioma growth by tumor-specific activation of double-stranded RNA-dependent protein kinase PKR", Nature Biotechnology, vol. 20, pp. 895-900, Sep. 2002.
Silverman et al., "Oligonucleotide Probes for RNA-Targeted Fluorescence in Situ Hybridization." *Advances in Clinical Chemistry* 43 (2007): 79-115.
Silverman et al., "Quenched Autoligation Probes Allow Discrimination of Live Bacterial Species by Single Nucleotide Differences in rRNA." *Nucleic Acids Research* 33.15 (2005): 4978-4986.
Siolas et al., "Synthetic shRNAs as Potent RNAi Triggers." *Nature Biotechnology* 23.2 (Feb. 2005): 227-231.
Sokol et al., "Real time detection of DNA●RNA hybridization in living cells", Proc. Natl. Acad. Sci. USA, vol. 95, pp. 11538-11543, Sep. 1998.
Storhoff et al., "One-pot colorimetric differentiation of polynucleotides with single base imperfections using gold nanoparticles," J. Am. Chem. Soc., 120, pp. 1959-1964, 1998.
Sun et al., "Side Chain Chemistry Mediates Backbone Fragmentation in Hydrogen Deficient Peptide Radicals." *Journal of Proteome Research* 8 (2009) 958-966.
Supplementary European Search Report from PCT/US2005/009471, dated May 6, 2008.
Takei et al., "A Small Interfering RNA Targeting Vascular Endothelial Growth Factor as Cancer Therapeutics." *Cancer Research* 64. (May 15, 2004): 3365-3370.
Tani et al., "Synthesis and Structural Analysis of 2-Quinuclidonium Tetrafluoroborate." *Nature* 441 (Jun. 8, 2006) 731-734.
Thomas et al., "Photoaffinity Cross-Linking and RNA Structure Analysis." *Methods in Enzymology* 318 (2000) 136-147.
Thompson, N.L.; Lieto, A.M., and Allen, N.W. "Recent advances in fluorescence correlation spectroscopy." Curr. Opin.Struct. Biol., 12, 2002.
Tijsterman et al., "Dicers at RISC: The Mechanism of RNAi", Cell, vol. 117, pp. 1-3, 2004.
Turberfield, et al., "DNA fuel for free-running nanomachines," Physical Review Letters, vol. 90, No. 11, pp. 118102-1-118102-4, Mar. 21, 2003.
Tuerk et al., "Systematic Evolution of Ligands by Exponential Enrichment: RNA Ligands to Bacteriophage T4 DNA Polymerase," Science 249, pp. 505-510, 1990.

(56) References Cited

OTHER PUBLICATIONS

Turk, Greg and Levoy, Marc. "Zippered polygon meshes from range images." In SIGGRAPH, pp. 311-318, 1994.
Tyagi et al., "Molecular Beacons: Probes that Fluoresce upon Hybridization," Nature Biotechnology 14, pp. 303-308, 1996.
U.S. File History printed for U.S. Appl. No. 11/087,937, filed Mar. 22, 2005, entitled "Hybridization Chain Reaction".
U.S. File History for U.S. Appl. No. 12/611,875, filed Nov. 3, 2009, entitled "Hybridization Chain Reaction".
U.S. File History for U.S. Appl. No. 11/371,346, filed Mar. 7, 2006, entitled "Hybridization Chain Reaction Amplification for in Situ Imaging".
U.S. File History for U.S. Appl. No. 12/790,379, filed May 28, 2010, entitled "Hybridization Chain Reaction Amplification for in Situ Imaging".
U.S. File History for U.S. Appl. No. 11/371,347, filed Mar. 7, 2006, entitled "Colorimetric Readout of Hybridization Chain Reaction".
U.S. File History for U.S. Appl. No. 11/544,306, filed Oct. 6, 2006, entitled "PKR Activation Via Hybridization Chain Reaction".
U.S. File History for U.S. Appl. No. 12/040,735, Feb. 29, 2008, entitled "Triggered RNAi".
U.S. File History for U.S. Appl. No. 12/152,893, filed May 16, 2008, entitled "A Versatile Nucleic Acid Hairpin Motif for Programming Biomolecular Self-Assembly Pathways".
U.S. File History for U.S. Appl. No. 12/395,489, filed Feb. 27, 2009, entitled "Triggered RNAi".
U.S. File History for U.S. Appl. No. 12/454,799, filed May 22, 2009, entitled "Compositions and Methods for Detecting Analytes".
U.S. File History for U.S. Appl. No. 12/467,755, May 18, 2009, entitled "Shielded Cross-Linking Probes".
U.S. File History for U.S. Appl. No. 12/454,743, filed May 22, 2009, entitled "Triggered RNAi".
U.S. File History for U.S. Appl. No. 13/186,228, filed Jul. 19, 2011, entitled "Biomolecular Self-Assembly".
U.S. File History for U.S. Appl. No. 13/186,315, filed Jul. 19, 2011, entitled "Triggered Molecular Geometry Based Bioimaging Probes".
Van De Corput et al., "Sensitive mRNA Detection by Fluorescence in Situ Hybridization Using Horseradish Peroxidase-labeled Oligodeoxynucleotides and Tyramide Signal Amplification," J. Histochem Cytochem, 46(11), pp. 1249-1259, 1998.
Venkataraman et al., "An Autonomous Polymerization Motor Powered by DNA Hybridization." *Nature Nanotechnology* 2 (Aug. 2007): 490-494.
Venkataraman et al. "Selective Cell Death Mediated by Small Conditional RNAs", Proc Natl Acad Sci USA, early edition, approved Jul. 21, 2010, p. 1-6.
Venkataraman et al. Abstract of "Selective Cell Death Mediated by Small Conditional RNAs", Proc Natl Acad Sci USA, early edition, http://www.pnas.org/content/early/2010/09/01/1006377107.abstract.
Vermeulen et al., "The contributions of dsRNA structure to Dicer specificity and efficiency", RNA, vol. 11, pp. 674-682, 2005.
Vodovozova et al., "Photoaffinity Labeling and Its Application in Structural Biology." *Biochemistry* (Moscow) 72.1 (2007): 1-20.
Volker, et al., "Conformational energetics of stable and metastable states formed by DNA triple repeat oligonucleotides: implications for triplet expansion diseases," PNAS, vol. 99, No. 23, pp. 14700-14705, Nov. 12, 2002.
Von Kiedrowski, "A Self-Replicating Hexadeoxynucleotide", Agnew. Chem. Int. Ed. Engl., vol. 25, No. 10, pp. 932-935, 1986.
Voorhoeve et al., "Knockdown Stands Up.:" *Trends in Biotechnology* 21.1 (Jan. 2003) 2-4.
Wagner et al., "Transferrin-Polycation Conjugates as Carriers for DNA Uptake into Cells", Proceedings of the National Academy of Sciences of the United States of America, vol. 87, pp. 3410-3414, May 1990.
Wassarman et al., "Psoralen Crosslinking of Small RNAs in vitro." *Molecular Biology Reports* 17 (1993): 143-151.
White et al., "The Catalytic Asymmetric Total Synthesis of Elatol." *Journal of American Chemical Society* 130.3 (2008): 810-811.

Wijen et al., "The in vivo Genetic Activity Profile of the Monofunctional Nitrogen Mustard 2-Chloroethylamine Differs Drastically from its Bifunctional Counterpart Mechlorethamine." *Carcinogenesis* 21.10 (2000) 1859-1867.
Wilkie et al., "Transcribed genes are localized according to chromosomal position within polarized *Drosophila* embryonic nuclei," Current Biology, 9, pp. 1263-1266, 1999.
Williams, B.R.G., "PKR; a sentinel kinase for cellular stress", Oncogene, vol. 18, pp. 6112-6120, 1999.
Willis, M.C., et al. Photocross-linking of 5-Iodouracil-Substituted RNA and DNA to Proteins. Science, 1993. 262: p. 1255-1257.
Winfree et al., "Design and self-assembly of two-dimensional DNA crystals", Nature, vol. 394, pp. 539-544, Aug. 6, 1998.
Winfree, E. Algorithmic Self-Assembly of DNA, Ph.D. thesis. Thesis, California Institute of Technology, 1998.
Winfree, E. "On the computational power of DNA annealing and ligation." Computation and Neural Systems, California Institute of Technology, May 25, 1995.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Yan et al., "DNA-Templated Self-Assembly of Protein Arrays and Highly Conductive Nanowires", Science, vol. 301, pp. 1882-1884, Sep. 26, 2003.
Yin et al., "Programming biomolecular self-assembly pathways", Nature, vol. 451, pp. 318-323, Jan. 17, 2008.
Yin, P.; Hartemink, "Theoretical and practical advances in genome halving." A.K. Bioinformatics 2005, 21, 869-879.
Yin, P.; Hariadi, R.; Sahu, S.; Choi, H.M.T.; Park, S.H.; :LaBean, T.H.; J.H. Reif, "Programming DNA Tube Circumferences." Science 2008, 321, 824-826.
Yin P.; Yan, H.; Daniell, X.; Turberfield, A.J.; Reif, J. "A Unidirectional DNA Walker that Moves Autonomously along a Track." Angewandte Chemie International Edition 2004, 43, 4906-4911.
Yin, P.; Turberfield, A.J.; Reif, J.H. "Designs of Autonomous Unidirectional Walking DNA Devices." In Proc. $10^{th}$ International Meeting on DNA computing; 2004.
Yoshimura et al., "Interstrand Photocrosslinking of DNA via p-carbamoylvinyl Phenol Nucleoside." *Bioorganic & Medicinal Chemistry Letters* 15 (2005): 1299-1301.
Yurke et al., "A DNA-fuelled molecular machine made of DNA", Letters to Nature, vol. 406, pp. 605-608 (Aug. 10, 2000).
Zadeh et al., "Software News and Updates NUPACK: Analysis and Design of Nucleic Acid Systems", Journal of Computational Chemistry, vol. 32, No. 1, pp. 170-173, 2011.
Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zhang et al., Targeted Gene Silencing by Small Interfering RNA-Based Knock-Down Technology, Current Pharmaceutical Biotechnology, vol. 5, pp. 1-7, 2004.
Zheng et al., "Activation of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zuker et al., "Optimal computer folding of large RNA sequence using thermodynamics and auxiliary information," Nucleic Acids Research, vol. 9, No. 1, pp. 133-147, 1981.
Seeman, et al., Nucleic Acid Nanostructures: Bottom Up Control of Geometry on the Nanoscale, Reports on Progress in Physics, 68 :237 (2005).
Stemmer, et al, Single Step Assembly of a Gene and Entire Plasmid from Large Numbers of Oligodeoxyribonnucleotides. Gene, vol. 164, pp. 49-53 (1995).
Tyagi, et al., Multicolor Molecular Beacons for Allele Discrimination, Nature Biotechnology vol. 16, pp. 49-53, Jan. 1998.
Communication Article 94(3) EPC from Application No. 08755764. 1, dated Nov. 7, 2012.

(56) References Cited

OTHER PUBLICATIONS

File History of U.S. Appl. No. 12/040,735.
Final Office Action dated Mar. 7, 2013 for U.S. Appl. No. 13/016,811.
Final Office Action dated Jun. 28, 2013 for U.S. Appl. No. 13/186,228.
Office Action dated Aug. 2, 2013 for U.S. Appl. No. 13/186,315.
Office Action dated Jan. 24, 2013 for U.S. Appl. No. 13/186,228.
Notice of Allowance dated Feb. 20, 2013 for U.S. Appl. No. 12/395,489.
Notice of Allowance dated Apr. 4, 2013 for U.S. Appl. No. 13/363,022.
Notice of Allowance dated May 24, 2013 for U.S. Appl. No. 13/016,811.
Notice of Allowance dated Oct. 23, 2013 in U.S. Appl. No. 13/016,811.
Bath et al., "DNA nanomachines", Nature Nanotechnology, vol. 2, pp. 275-284, May 2007.
Bonnet et al. Thermodynamic basis of the enhanced specificity of structured DNA probes, Proc. Natl. Acad. Sci. USA vol. 96 (May 1999), pp. 6171-6176.
Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.
Gasparro et al., Site-specific targeting of psoralen photoadducts with a triple helix-forming oligonuicleotide: characterization of psoralen monoadduct and crosslink formation. Nucleic Acids Research 22 (1994), pp. 2845-2852.
Evanko, "Hybridization chain reaction", Nature Methods, vol. 1, No. 3, pp. 186-187, Dec. 2004.
Jayasena, "Aptamers: An Emerging Class of Molecules That Rival Antiodies in Diagnostics", Clinical Chemistry, vol. 45, No. 9, pp. 1628-1650, 1999.
Li et al., A new class of homogenous nucleic acid probes based on specific displacement hybridization, Nucleic Acids Research, vol. 30, No. 2e5 (2002), pp. 1-9.
Office Action dated Nov. 9, 2010 for U.S. Appl. No. 12/040,735.
Office Action dated Apr. 2, 2014 for U.S. Appl. No. 12/467,755.
Office Action dated Jan. 27, 2014 for U.S. Appl. No. 13/186,315.
Peng et al., Facile SNP detection using bifunctional, cross-linking oligonucleotide probes, Nucleic Acids Research vol. 36 No. 5e31 (2008), pp. 1-7.
Piston et al., "Fluorescent protein FRET: the good, the bad and the ugly", Trends Biochem Sci., Sep. 2007, vol. 32, No. 9, pp. 407-414.
Shaner et al., "A guide to choosing fluorescent proteins", Nature Methods, vol. 2, No. 12, pp. 905-909, Dec. 2005.
Situma et al., "Immobilized molecular beacons: A new strategy using UV-activated poly(methyl methacrylate) surfaces to provide large fluorescence sensitivities for reporting on molecular association events." Analytical Biochemistry 363 (2007) 35-45.
Yurke, et al., "A DNA-fuelled molecular machine made of DNA" Nature, vol. 406, Aug. 10, 2000, pp. 605-608.

* cited by examiner

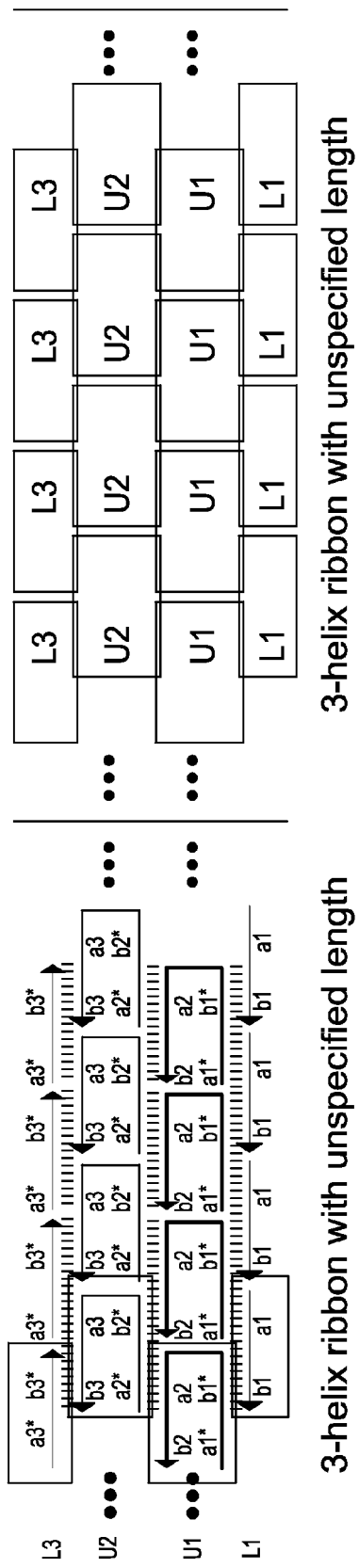
FIG. 1A
3-helix ribbon with unspecified length
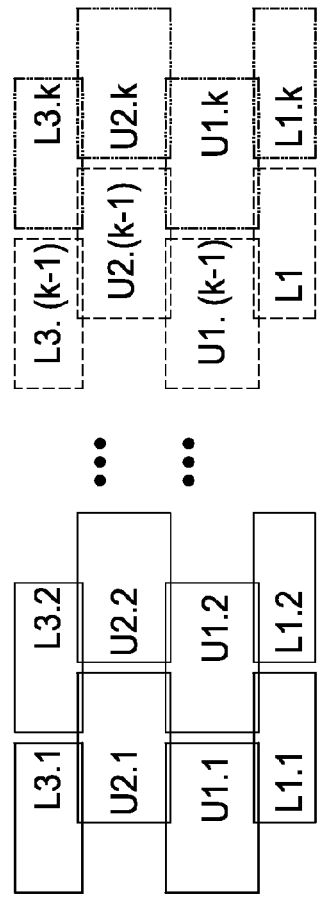
FIG. 1B
3-helix ribbon with unspecified length
FIG. 1C
3-helix ribbon with length of k tiles

SELF-ASSEMBLED POLYNUCLEOTIDE STRUCTURE

CROSS-REFERENCE TO RELATED APPLICATIONS

The present application claims priority under 35 U.S.C. §119(e) to U.S. Provisional Application No. 61/366,082, filed on Jul. 20, 2010, which is herein expressly incorporated by reference in its entirety.

BACKGROUND OF THE INVENTION

1. Field of the Invention

The present application relates generally to polynucleotide structures, such as nucleic acid ribbons and nucleic acid tubes; methods for making those polynucleotide structures; and methods of building two-dimensional/three-dimensional objects using the nucleic acid ribbons and tubes.

2. Description of the Related Art

DNA has been proposed to be a suitable construction material to build synthetic lattices that template proteins into periodic arrays for crystallization. The idea for assembling synthetic DNA structures includes: encoding sequence complementarity in synthetic DNA strands in a suitable fashion such that by pairing up the complementary segments, DNA strands self-organize into a prescribed structure. A number of DNA structures have been created, such as ribbons, tubes, lattices, arbitrary 2D and 3D shapes. See, e.g., Seeman, Nature 421:427-431 (2003); Feldkamp & Niemeyer, Angewandte Chemie International Edition, 45:1856-1876 (2006). Besides static structures, dynamic structures that compute, move, and grow have also been demonstrated. Seeman; Feldkamp & Niemeyer; Bath & Turberfield, Nature Nanotechnology 2:275-284(2007). Additionally, synthetic DNA/RNA structures and devices have been used to direct material arrangements (e.g., proteins (Yan et al., Science 301(5641):1882-1884 (2003)), gold nanoparticles (Le et al., Nano Lett., 4:2343-2347 (2004)), quantum dots (Sharma et al., Angew. Chem. Int. Ed., 47:5157-5159 (2008), and carbon nanotubes (Chen et al., J. Am. Chem. Soc., 129 (2007))) and to facilitate NMR protein structure determination (Douglas et al., Proc. Natl. Acad. Sci. USA, 104, 6644-6648 (2007)). Synthetic DNA/RNA structures are also thought to be useful in probing and manipulating cellular processes for bioimaging and therapeutic applications.

SUMMARY OF THE INVENTION

In some embodiments, a polynucleotide structure or composition is provided. The structure or composition can comprise a first species, a second species, a third species, a fourth species, a fifth species, and, a sixth species. In some embodiments, the first, the second, and the third species are hybridized to form a first column. In some embodiments, the fourth, the fifth, and the sixth species are hybridized to form a second column. In some embodiments, the first column is hybridized to the second column, providing a length to the polynucleotide structure, and wherein the sequence of the first species is different from the sequence of the fourth species.

In some embodiments, a method of making a polynucleotide structure is provided. The method can include providing a first species, a second species, a third species, a fourth species, a fifth species, and a sixth species. In some embodiments, the sequence of the first species is different from the sequence of the fourth species. In some embodiments, one can also maintain the first, the second, the third, the fourth, the fifth, and the sixth species in conditions that 1) allow the first, second, and third species to hybridize to form a first column, 2) allow the fourth, fifth, and sixth species to hybridize to form a second column, and 3) allow the first column to hybridize to the second column to provide a polynucleotide structure of a defined and/or desired length.

BRIEF DESCRIPTION OF THE DRAWINGS

FIGS. 1A-1C depict some embodiments of nucleic acid ribbons made from a collection of species. FIG. 1A is schematic illustration of a 3-helix ribbon with unspecified length, showing flexible binding sections. FIG. 1B is schematic illustration of a 3-helix ribbon with unspecified length. FIG. 1C is schematic illustration of a 3-helix ribbon with length of k tiles.

FIG. 4A is a schematic illustration of an untreated 4-helix nucleic acid tube. FIG. 4B is a schematic illustration of a 4-helix nucleic acid tube with self-ligated species. FIG. 4B is a schematic illustration of a 4-helix nucleic acid tube in which the species are cross linked.

FIG. 9A is a schematic illustration of making a nucleic acid tetrahedron using DNA origami joints. FIG. 9B is a schematic illustration of making a nucleic acid tetrahedron using nucleic acid ribbons or tubes that comprise two single-stranded sticky ends at either end of the ribbons or tubes.

DETAILED DESCRIPTION

Figure 2:
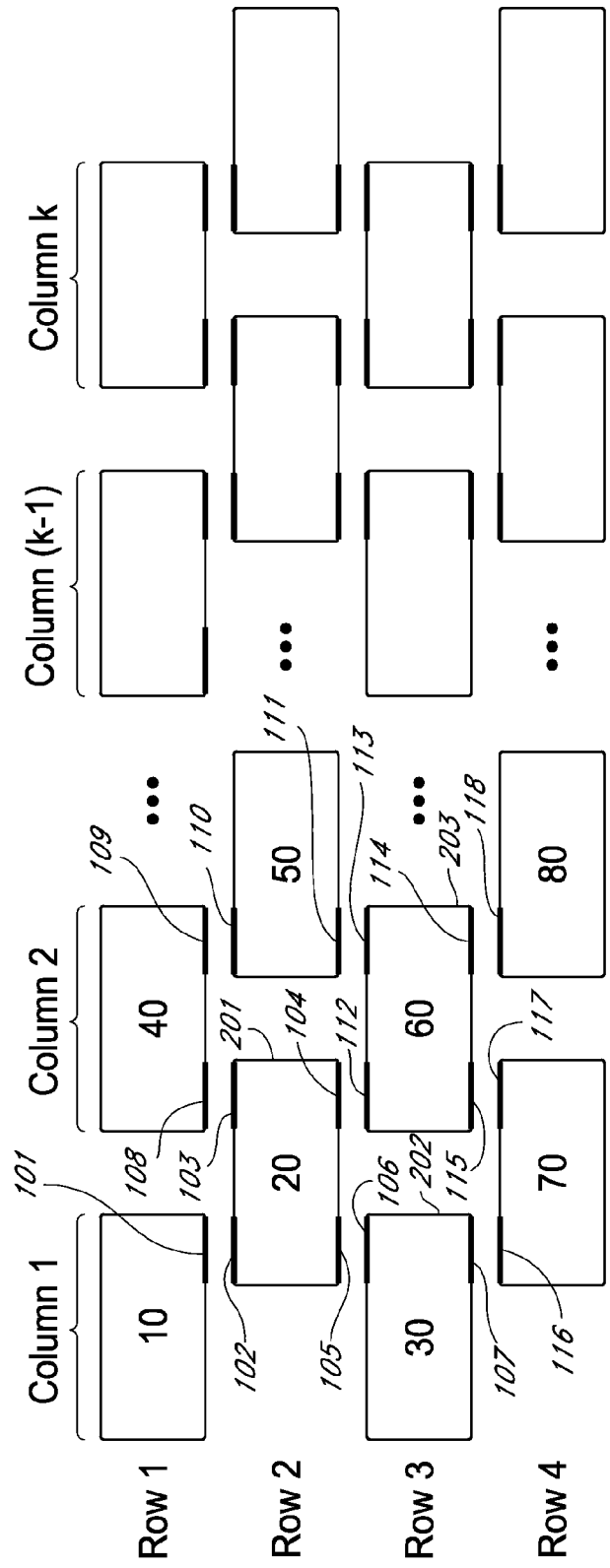
FIG. 2 depicts some embodiments of nucleic acid ribbons of length of k columns.

As disclosed herein, polynucleotide structures can be synthesized using single stranded nucleotide species. In some embodiments, the polynucleotide structure is a nucleic acid ribbon or a nucleic acid tube. While it is currently possible to provide nucleic acid tile based structures of a defined or desired width, there is currently little in the way to being able to provide for tile based structures with a desired or defined length. In some embodiments, the polynucleotide structure and/or methods provided herein are of, or provide for, a predetermined length. In some embodiments, the polynucleotide structure is a two-dimensional or three-dimensional (2D/3D) object comprising the nucleic acid ribbons and/or nucleic acid tubes described herein. In some embodiments, the present application relates to methods for making the polynucleotide structures described herein.

Definition

Unless defined otherwise, technical and scientific terms used herein have the same meaning as commonly understood by one of ordinary skill in the art to which this invention belongs.

As used herein, the term "species" refers to a single-stranded polymeric form of nucleotides of any length. A species can be naturally occurring polynucleotides, synthetic polynucleotides, or a combination thereof. A polynucleotide can also include analogs of DNA or RNA having modification(s) to sugars, the heterocyclic bases and/or the backbone. For example, a polynucleotide can include methylated nucleotide(s), and modified purine and/or pyrimidine bases. Examples of modified backbone include, but are not limited to, phosphorothioates; phosphorodithioates, where both of the non-bridging oxygens are substituted with sulfur; phosphoroamidites; alkyl phosphotriesters; boranophosphates; achiral phosphate derivatives, such as 3'-O'-5'-S-phosphorothioate, 3'-S-5'-O-phosphorothioate, 3'-CH$_2$-5'-O-phosphonate and 3'-NH-5'-O-phosphoroamidate; and peptide nucleic acids in which the entire ribose phosphodiester backbone is replaced with a peptide linkage. In some embodiments, modifications of the backbone, sugars and/or heterocyclic bases may increase stability and/or binding affinity of the species. A species can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), L-DNA, etc.

The species disclosed herein can be of various lengths. In some embodiments, the species can be about 21, 42, 63, 84, 105, or 21n nucleotides in length. In some embodiments, the species can be about 21 nucleotides in length. In some embodiments, the species can be about 42 nucleotides in length. In some embodiments, for a full species that contains four concatenated sticky ends, I, II, III, and IV, the total length of I and II is 21 nucleotides, and the total length of III and IV is 21 nucleotides, and hence the total length of the full species is 42 nucleotides. In some embodiments, the total length of the sticky ends I and II can be the integer number most close to 10.5*n, where n=1, 2, 3, 4, 5, . . . , 10, and the total length of III and IV can be the integer number most close to 10.5*n, where n=1, 2, 3, 4, 5, . . . , 10, and hence the total length of the full species is about 21*n, where n=1, 2, . . . , 10. In some embodiments, for RNA motifs, for a full species that contains four concatenated sticky ends, I, II, III, and IV, the total length of I and II is 22 nucleotides, and the total length of III and IV is 22 nucleotides, and hence the total length of the full species is 44 nucleotides. In some embodiments, the total length of the sticky ends I and II can be the integer number most close toll*n, where n=1, 2, 3, 4, 5, . . . , 10, and the total length of III and IV can be the integer number most close toll*n, where n=1, 2, 3, 4, 5, . . . , 10, and hence the total length of the full species is about 21*n, where n=1, 2, . . . , 10. In some embodiments, the value 10.5 and/or 11 can be adjusted to the number of bases in a full helical turn of that material. Thus, in some embodiments, 10.5 and/or 11 can be substituted by the appropriate number of bases required for a full helical turn for that material.

As used herein, the term "complementary" and/or grammatical equivalents thereof refer to the nucleotide base-pairing interaction of one nucleic acid with another nucleic acid that results in the formation of a duplex, triplex, or other higher-ordered structure. In some embodiments, the nucleic acids are similar enough in complementarity between sequences to permit hybridization under various stringency conditions. As will be appreciated by persons skilled in the art, stringent conditions are sequence-dependent and are different in different circumstances. For example, longer fragments may require higher hybridization temperatures for specific hybridization than short fragments. Because other factors, such as base composition and length of the complementary strands, presence of organic solvents, and the extent of base mismatching, may affect the stringency of hybridization, the combination of parameters can be more important than the absolute measure of any one parameter alone. In some embodiments, hybridization can be made to occur under high stringency conditions, such as high temperatures or 0.1×SCC. Examples of high stringent conditions are known in the art; see e.g., Sambrook et al., Molecular Cloning: A Laboratory Manual, 2d Edition, 1989, and Short Protocols in Molecular Biology, ed. Ausubel et al., both of which are hereby incorporated by reference. In general, increasing the temperature at which the hybridization is performed increases the stringency. As such, the hybridization reactions described herein can be performed at a different temperature depending on the desired stringency of hybridization. Hybridization temperatures can be as low as or even lower than 5° C., but are typically greater than 22° C., and more typically greater than about 30° C., and even more typically in excess of 37° C. In other embodiments, the stringency of the hybridization can further be altered by the addition or removal of components of the buffered solution. In some embodiments, hybridization is permitted under medium stringency conditions. In other embodiments, hybridization is permitted under low stringency conditions. In some embodiments, a nucleic acid sequence is perfectly complementary to a capture nucleic acid or other molecule with which it binds. In other embodiments, one or more mismatches are present between the hybridized molecules or hybridized portions of molecules.

As used herein, the term "tile" refers to a modular building unit for polynucleotide assembly. In general, a tile has binding sites or binding sections that mediate its interaction with other tiles. In some embodiments, as disclosed herein, the tile is a single-stranded polynucleotide. In some embodiments, the tiles are multi-stranded.

As used herein, the term "single stranded tile system" refers to a polynucleotide structure assembly system using tiles that are single-stranded polynucleotides. Such single stranded molecules are denoted as "species" herein.

A "species" or "single stranded nucleic acid species" as used herein denotes a single-stranded polynucleotide that can be used to hybridize to other single-stranded polynucleotides to form a two or three dimensional nucleic acid structure. Any natural, artificial, modified and/or derivatized nucleic acid can be employed as a species. In some embodiments, the nucleic acids are or include RNA, DNA, PNA, Z-DNA, A-DNA, B-DNA, Z-RNA morpholino-nucleic acid, LNA (locked nucleic acid)glycol nucleic acid, threose nucleic acid, etc. The term "species" is also referenced as a "single-stranded tile species".

As used herein, a "multi-stranded tile system" refers to a polynucleotide structure assembly system using tiles (or species). In some embodiments, the multi-stranded tile system has (1) a relatively rigid core composed of primarily double-stranded DNA helices and (2) a number of single-stranded "sticky ends" that allow for specific binding with other tiles to guide the crystal formation. In some embodiments, during the annealing process, nucleic acid strands first assemble into tiles with rigid cores bearing affinity encoding sticky ends; the tiles then form lattice structures by preferentially matching their sticky ends. In some embodiments, the multi-stranded tile system does not have a relatively rigid core composed of primarily double-stranded DNA helices. In some embodiments, the multi-stranded tile system does not have a number of single-stranded "sticky ends" that allow for specific binding with other tiles to guide the crystal formation.

As used herein in, the term "ribbon" refers to a form of the polynucleotide structure. In a polynucleotide ribbon, each edge of the ribbon represents a sugar-phosphate backbone, and with one edge having a direction opposite to the other. For example, in a double-stranded DNA, the two antiparallel sugar-phosphate backbones of the DNA molecular can wind up around the central axis to form a 1-helix ribbon. As described herein, a polynucleotide ribbon can include various numbers of polynucleotide helices. In some embodiments, the ribbon includes 2 helices. In some embodiments, the ribbon includes 3 helices. In some embodiments, the ribbon includes 4 helices. In some embodiments, the ribbon includes 4 helices. In some embodiments, the ribbon include 5, 6, 7, 8, 9, 10, 11, 12, 13, 14, 15, 16, 17, 18, 19, 20, 21, 22, 23, 24, 25, 26, 27, 28, 29, 30, or more helices.

As used herein, the term "3-helix ribbon" refers to a helical form of a polynucleotide structure having 3 nucleic acid double-stranded helices.

As used herein, the term "row" refers to a unit formed by any number of species arranged in a direction along the growing dimension of the structure.

As used herein, the term "column" refers to a unit formed by any number of species arranged in a direction substantially perpendicular to the row.

As used herein, the terms "predetermined length," "desired length" and "defined length" are used interchangeably. In some embodiments, the predetermined length of the polynucleotide is determined by, for example, the kind and number of the species used to assemble the polynucleotide structure, and the hybridizations among the species. In some embodiments, the length of the polynucleotide is measured by the number of columns in a row. In some embodiments, the length of the polynucleotide is measured by the number of the species in a row. In some embodiments, the length of the polynucleotide is measured by the number of the nucleotides in a row.

As used herein, the term "binding section" refers to a portion of a species (or a tile) that is configured to hybridize to a complementary nucleic acid sequence of another species (or tile) in the polynucleotide structure. In some embodiments, a species has at least one, two, three, or four binding sections. In some embodiments, a species has at least one binding section. A binding section of a species is configured such that it specifically hybridizes to another species under a hybridization condition. In some embodiments, the binding section of a species is configured such that it specifically hybridizes to only one other species under a hybridization condition.

As used herein, the term "linkage region" refers to a portion of the species (e.g., nucleic acid sequence) that is not bound to any of the other species in the polynucleotide structure. In some embodiments, this allows the nucleic acid to form part of a "loop" or "U" shape. As discussed above, some species can have at least one linkage region. In some embodiments, the linkage region is a phosphate backbone. In some embodiments, the linkage region is between two binding sections of a species.

The term "different" as used herein in regard to a first species and a subsequent species in a given row denotes that there is a difference in the sequence and/or hybridization properties of the first species and the subsequent species. Two species are different when the sequences that the first species will hybridize to are different from the sequences that the second species will hybridize to. In some embodiments, the difference is such that the sequences are not identical, e.g., 1, 2, 3, 4, 5, 6, 7, 8, 9, 10, 12, 15, 20, 25, 30, 35, 40, 45, 50, 60, 70, 80, 90, 95, 98, 99 percent or more of the nucleotides are different between the sequences of the two species. In some embodiments, the areas of sequence comparison for determining "difference" are just the binding sections between the two species. In some embodiments, two species are different if the first species will bind to species that are different from the species that the subsequent species will bind to.

DNA Structures

Approaches for constructing static DNA structures largely fall into two categories: the folding of a long strand or the assembly of modular units called tiles. Fu & Seeman, Biochemistry 32: 3211-3220 (1993); Winfree et al., Nature 394, 539-544 (1998). The first approach, now known as DNA origami (Rothemund, Nature 440: 297-302 (2006)), has produced 2D (Rothemund, 2006) and 3D (Douglas et al., Nature 459:414-418 (2009); Dietz, Science 325: 725-730 (2009)) shapes of remarkable complexity. For example, a long natural scaffold strand (e.g., the 7 kilobase M13 virus genome) can be folded by hundreds of short synthetic "staple" strands into a prescribed shape of about 100 nanometer diameter. However, folding alone is not suitable for constructing larger objects, e.g., objects with diameter of 1-10 micrometer. First, it is difficult to obtain or synthesize much longer scaffold strands. Additionally, folding a much longer scaffold into complex 3D shapes necessarily entails long annealing time, and is vulnerable to be kinetically trapped in unintended local minimum on the free energy landscape that corresponds to misfolded structures. Indeed, extending the origami from 2D to 3D requires the annealing time to be increased from <2 hours (Rothemund, 2006) to a week (Douglas et al., 2009). Modular and hierarchical approaches using DNA tiles have been utilized, for example (a DNA origami itself can be viewed as a tile, i.e. a modular building block with well defined binding sites that mediate its interaction with other tiles. Many DNA tiles See, e.g., Winfree 1998, Yan et al. 2003; Mitchell et al. J. Am. Chem. Soc., 126:16342-16343 (2004); Liu et al. Proc. Natl. Acad. Sci. USA, 101:717-722 (2004); Rothmund et al., J. Am. Chem. Soc., 126:16344-16353 (2004); Mathieu et al., Nano Lett., 5:661-665 (2005); Park et al., Nano Lett., 5:693-696 (2005); Liu et al., Angew. Chem. Int. Ed., 45, 1942-1945 (2006); Kuzuya et al., Nano Lett., 7:1757-1763 (2007); Schulman & Winfree, Proc. Natl. Acad. Sci. USA, 104: 15236-15241 (2007); Lin et al., ChemPhysChem (2006) ChemPhysChem 2006, 7, 1641-1647 have been generated so far, for which the researchers chose the largest tile, i.e. the origami tile with >15 kilobases, as a promising candidate for constructing larger objects. Using such tiles, moderate increases in scale have been achieved, e.g., an icosohedron of 100 nm diameter made from the trimerization of three DNA orgiami tiles (Douglas et al., 2009). While construction with large origami tiles remains a promising route to be explored, it has now been realized that another route using tiny tiles is more promising and interesting.

As described in the present application, large 2D/3D objects, such as the objects with 1-100 μm diameter can be made using single stranded polynucleotide species, for example a single stranded species of 21 or 42 nucleotides in length. Unlike traditional multistranded tiles composed of a rigid structural "core" and several binding sites or "sticky ends" (see, e.g., FIGS. 1A and 1B), the "species" system described and used herein need not have the rigid core and can contain flexible sticky ends, which can be concatenated into a single strand. Compared with multi-stranded tiles, species (e.g., single-stranded polynucleotides) can be dramatically simpler, structurally flexible, more robust and thermal stable, and suitable for constructing large scale, complex structures with low error rates.

As described herein, the species can be used in assembling polynucleotide structures, such as nucleic acid ribbons and nucleic acid tubes with programmable diameters as well as having programmable lengths. These nucleic acid ribbons and nucleic acid tubes can be used as modular building blocks to construct large 2D/3D polynucleotide objects.

Single-Stranded Polynucleotide "Species" (Single Stranded Tile (SST)) Motif

A traditional DNA tile is a compact structure woven from a number of component DNA strands (see, e.g., FIGS. 1A and 1B). In general, a traditional DNA tile has (1) a relatively rigid core composed of primarily double-stranded DNA helices and (2) a number of single-stranded "sticky ends" that allow for specific binding with other tiles to guide the crystal formation. The tile provides a layer of powerful structural abstraction between the individual component DNA strands and the final assembled crystal structures. During the annealing process, DNA strands first assemble into tiles with rigid cores bearing affinity encoding sticky ends; the tiles then form lattice structures by preferentially matching their sticky ends.

Unlike traditional multistranded tiles, "species" (single-stranded tiles, or SSTs) need not have the rigid core and contain flexible sticky ends, which can be concatenated into a single strand. In some embodiments. compared with multi-stranded tiles, species are uniquely suitable for constructing large scale, complex structures with low error rates. First, compared with traditional multiple-stranded tile systems, the species system requires much less, and often shorter component strands. Second, in traditional multi-strand tile systems, defective, partially-assembled tiles can often be incorporated into the growing aggregate; the species system, where each tile is a single strand, can avoid this problem. Third, the flexible single-stranded form of species permits it to dynamically correct assembly errors: correct tiles can displace incorrect or defective ones via strand displacement. Yurke et al., Nature, 406:605-608 (2000); Rothemund, 2006.

In some embodiments, the species motif can be 42-nucleotides in length. In some embodiments, the species motif can include four concatenated sticky ends (from the 5' end to the 3' end of the species, they are named the first, the second, the third, and the fourth sticky ends in order). In some embodiments, the first and the second sticky ends together contain 21 nucleotides, and the third and the fourth sticky end together contain 21 nucleotides, and hence the species has a total length of 42 nucleotides.

In some embodiments, the species motif on the upper and lower boundary of the ribbon only contains two sticky ends, and hence can be of 21 nucleotides in length, for example, the "L" species in FIG. 1. In some embodiments, the species motif can be of 21 nucleotides in length. In some embodiments, the species motif can include two concatenated sticky ends. By pairing up complementary sticky ends, species tiles can be arranged to form DNA lattices composed of parallel DNA helices connected by single-stranded linkages. In some embodiments, the inner or "U" species (in FIG. 1) involve 4 concatenated sticky ends. In some embodiments, the U species are termed inner species. In some embodiments, the L species are termed boundary species. Not all embodiments require a boundary species (e.g., for tubes, the U species can be employed without a L species).

In some embodiments, for a full species that includes four concatenated sticky ends, I, II, III, and IV, the total length of I and II is 21 nucleotides, and the total length of III and IV is 21 nucleotides, and hence the total length of the full species is 42 nucleotides. In some embodiments, the total length of the sticky ends I and II can be the integer number most close to 10.5*n, where n=1, 2, 3, 4, 5, 6, 7, 8, 9, 10, etc. and the total length of III and IV can be the integer number most close to 10.5*n, where n=1, 2, 3, 4, 5, 6, 7, 8, 9, 10, etc, and hence the total length of the full species is about 21*n, where n=1, 2, 3, 4, 5, 6, 7, 8, 9, 10, etc.

In some embodiments, for RNA motifs, for a full species that contains four concatenated sticky ends, I, II, III, and IV, the total length of I and II is 22 nucleotides, and the total length of III and IV is 22 nucleotides, and hence the total length of the full species is 44 nucleotides. In some embodiments, the total length of the sticky ends I and II can be the integer number most close toll*n, where n=1, 2, 3, 4, 5, 6, 7, 8, 9, 10, etc. and the total length of III and IV can be the integer number most close toll*n, where n=1, 2, 3, 4, 5, 6, 7, 8, 9, 10, etc. and hence the total length of the full species is about 21*n, where n=1, 2, 3, 4, 5, 6, 7, 9, 10, etc.

In some embodiments, the value which is multiplied by "n" is the number of bases in a full helical turn of that material. Thus, the number can change according to the particular nucleotide being employed. Thus, in some embodiments, the 10.5 and/or 11 noted above can be substituted by the appropriate number of bases required for a full helical turn for that material.

Nucleic Acid Ribbons and Tubes

FIG. 1C and FIG. 2 depict some embodiments of nucleic acid ribbons made from a collection of species.

In some embodiments, the nucleic acid ribbon shown in FIG. 2 comprises species 10, 20, 30, 40, 50, 60, 70 and 80. In some embodiments, species 10, 20, 30 and 70 are hybridized to form a first column. In some embodiments, species 40, 50, 60 and 80 are hybridized to form a second column. In some embodiments, the first column is hybridized to the second column, providing a length to the SST ribbon structure. Each of the species comprises at least one binding section (e.g., binding sections 101-118) to bind to at least one of the species in the same column or in a different column. For example, as shown in FIG. 2, species 10 has binding section 101; species 20 has binding sections 102, 103, 104 and 105; species 30 has binding sections 106 and 107; species 40 has binding sections 108 and 109; species 50 has binding sections 110 and 111; species 60 has binding sections 112, 113, 114 and 115; species 70 has binding sections 116 and 117; and species 80 has binding section 118. A species can also have at least one linkage region composed of 0 base, e.g., just the phosphate backbone of the DNA strand. For example, species 20 has a linkage region 201, species 30 has a linkage region 202, and species 60 has a linkage region 203. While each species or SST is shown in FIGS. 1C and 2 as a rectangle, this is for representative purposes only. While each species or SST is shown in FIGS. 1C and 2 as a rectangle, this is for representative purposes only. The underlying structure will still be that of single stranded nucleic acids (e.g., as shown in FIGS. 1A and 4A-4C).

In some embodiments of the nucleic acid ribbon shown in FIG. 2, species 10, 20 and 30 are hybridized to form Column 1, and species 40, 50 and 60 are hybridized to form Column 2. In some embodiments, species 10 and 40 form Row 1. In some embodiments, species 20 and 50 form Row 2. In some embodiments, species 30 and 60 form Row 3. In some embodiments, species 70 and 80 form Row 4. In some embodiments, by ensuring that the sequence for each species changes as one progress from column 1 to column 2, within a given row, one is able to ensure that one can control the length of the structure formed, as unique sequences will not allow random or continual extension. In some embodiments, species 70 are hybridized to species 30 to form a part of Column 1. In some embodiments, species 80 are hybridized to species 60 to form a part of Column 2.

In the embodiment of the nucleic acid ribbon shown in FIG. 2, species 10 binds to species 20 through hybridization between binding sections 101 and 102; species 20 binds to species 40 through hybridization between binding sections 103 and 108, binds to species 30 through hybridization between binding sections 105 and 106, binds to species 60 through hybridization between binding sections 104 and 112; species 30 binds to species 70 through hybridization between binding sections 107 and 116; species 40 binds to species 50 through hybridization between binding sections 109 and 110; species 50 binds to species 60 through hybridization between binding sections 111 and 113; species 60 binds to species 70 through hybridization between binding sections 115 and 117 and binds to species 80 through hybridization between binding sections 114 and 118. A species can also have a linkage region 201 and 202 (while shown as a rectangle in FIG. 2, there is no need for a linkage region on the opposite side of tiles 20 and 30, thus, in some embodiments, the tiles shown in FIG. 2 have the "U" shape of the tiles in FIGS. 4A and 4C). In some embodiments, the species comprises at least one linkage region. For example, species 20 has a linkage region 201, species 30 has a linkage region 202, and species 60 has a linkage region 203.

Additional Embodiments

In some embodiments, the species within each of the rows, as one moves from a first column to a second column can be different. Thus, in some embodiments, the sequence of species 10 and species 40 are different. In some embodiments, the sequence of species 20 and 50 are different. In some embodiments, the sequence of species 30 and 60 are different. In some embodiments, the sequence of species 70 and 80 are different. Because of one or more of these differences, the length of the ribbon or construct does not occur continuously or indefinitely, but occurs as dictated by the sequences of the binding sections.

In some embodiments, a polynucleotide structure descried herein can include a first, a second, a third, a fourth, a fifth; and a sixth species, where the first, the second, and the third species are hybridized to form a first column, where the fourth, the fifth, and the sixth species are hybridized to form a second column, where the first column is hybridized to the second column, providing a length to the polynucleotide structure. The sequence of each of the species can be the same or different from at least one of the other species in the polynucleotide structure. For example, the sequence of the first species can be different from the sequence of the fourth species; the sequence of the second species can be different from the sequence of fifth species; and/or the sequence of the third species can be different from the sequence of the sixth species. Also for example, the sequence of the first species can be different from the sequence of the second and the third species, and the sequence of the fourth species can be different from the sequence of the fifth and the sixth species. In some embodiments, the sequence of each of the first, the second, the third, the fourth, the fifth, and the sixth species is different from the sequence of at least one, at least two, or at least three of the other species. In some embodiments, the sequence of each of the first, the second, the third, the fourth, the fifth, and the sixth species is the same as the sequence of at least one of the other species. In some embodiments, the sequence of each of the first, the second, the third, the fourth, the fifth, and the sixth is independently different.

In some embodiments, each species in the polynucleotide structure can bind to, for example through hybridization, one or more species in the same column or in a different column. In some embodiments, the first species can bind to the second species; the second species can bind to the third species; the fifth species can bind to the forth and/or the sixth species; the sixth species can bind to the fifth species. In some embodiments, the second species can bind to the sixth species.

The polynucleotide structure can further comprise additional species. For example, the polynucleotide structure can further comprise a seventh and an eighth species, where the seventh species forms a part of the first column and the eighth species forms a part of the second column. In some embodiments, the seventh species can bind to the third and/or the sixth species. The eighth species can bind to the sixth species.

In some embodiments, the species in the polynucleotide structure described herein can be in various forms, for example, the species can be linear or "U" shaped. In some embodiments, each of the species is a linkage region and is U shaped (see FIG. 1A). In some embodiments, the first species (or the "boarder species" is linear. In some embodiments, the second and/or third species (or interior species") is a linkage region. In some embodiments, the fifth and/or sixth species is a linkage region. In some embodiments, the seventh and/or eighth species is a linkage region. In some embodiments, all the species in the polynucleotide structure are in the same form. In some embodiments, the seventh species is linear. In some embodiments, the eighth species is linear.

The species in the polynucleotide structure described herein can be of various lengths. For example, the species can be about 21, 42, 63, 84, 105, or 21 n nucleotides in length. In some embodiments, all the species in the polynucleotide structure are of the same length. In some embodiments, the species in linear form is about 21, 42, 63, or 84 nucleotides in length. In some embodiments, the species in linked form is about 42, 84 or 126 nucleotides in length. In some embodiments, the species is 21 nucleotides in length. In some embodiments, the species is 42 nucleotides in length. In some embodiments, the first and/or the seventh species are each 21 nucleotides in length. In some embodiments, the second, the third, the fifth, and/or the sixth species are each 42 nucleotides in length.

In some embodiments, for a full species that contains four concatenated sticky ends, I, II, III, and IV, the total length of I and II is 21 nucleotides, and the total length of III and IV is 21 nucleotides, and hence the total length of the full species is 42 nucleotides. In some embodiments, the total length of the sticky ends I and II can be the integer number most close to $10.5*n$, where $n=1, 2, 3, 4, 5, \ldots, 10$, and the total length of III and IV can be the integer number most close to $10.5*n$, where $n=1, 2, 3, 4, 5, \ldots, 10$, and hence the total length of the full species is about $21*n$, where $n=1, 2, \ldots, 10$.

In some embodiments, e.g., for RNA motifs, for a full species that contains four concatenated sticky ends, I, II, III, and IV, the total length of I and II is 22 nucleotides, and the total length of III and IV is 22 nucleotides, and hence the total length of the full species is 44 nucleotides. In some embodiments, the total length of the sticky ends I and II can be the integer number most close to $11*n$, where $n=1, 2, 3, 4, 5, \ldots, 10$, and the total length of III and IV can be the integer number most close to $11*n$, where $n=1, 2, 3, 4, 5, \ldots, 10$, and hence the total length of the full species is about $21*n$, where $n=1, 2, \ldots, 10$.

In some embodiments, the value 10.5 and/or 11 can be adjusted to the number of bases in a full helical turn of that nucleotide material. Thus, in some embodiments, 10.5 and/or 11 can be substituted by the appropriate number of bases required for a full helical turn for that nucleotide material.

The polynucleotide structure described herein can be of various lengths. For example, the polynucleotide can be about 2, about 5, about 10, about 50, about 100, about 200, about 300, about 400, about 500, about 600, about 700, about 800, about 900, about 1000, about 5000, about 10000, about 50000, about 100000, about 500000, about 1000000 columns in length, or any range between two of these values. In some embodiments, the polynucleotide is 2 to 1000000 columns in length. In some embodiments, the polynucleotide is 2 to 1000 columns in length.

The species described herein can be bonded, for example covalently, with at least one of the species in polynucleotide structure. In some embodiments, there is at least one covalent bond between at least two of the species. For example, there can be at least one covalent bond between the first and the seventh species. In some embodiments, the covalent bond comprises a disulfide bond.

In some embodiments, the polynucleotide structure is a nucleic acid tube. In some embodiment, the first column comprises a top and a bottom, where the top is adjacent to the bottom, so as to form a tube of the polynucleotide. The interaction between the top and the bottom is not limited in any way. The top and the bottom can interact, for example, by hybridization, by a covalent bond, including, for example, crosslinking. In some embodiments, the first and the seventh species interact so as to form a tube of the polynucleotide (e.g., see FIG. 4C)

In some embodiments, the species in the polynucleotide structure described herein can form rows. For example, the first and the fourth species can form a first row, the second and the fifth species can form a second row, and the third and the sixth species can form a third row. The polynucleotide structure can have various numbers of rows. For example, the polynucleotide structure can have about 1, about 3, about 4, about 5, about 6, about 8, about 10, about 20, about 30, about 40, about 50, about 60, about 70, about 80, about 90, about 100, about 150, or about 200 rows, or about 100,000 rows or any range between two of these values. In some embodiments, the polynucleotide comprises 1 to 100 rows. In some embodiments, all the species in the same row are linear. In some embodiments, all the species in the same row are linked sections.

Species

As discussed above, a species is a single-stranded polymeric form of nucleotides used for building the polynucleotide structures described herein. In some embodiments, each species has at least one region that is complementary to at least a portion of a second species, and thus can hybridize with the second species in a polynucleotide structure. In some embodiments, each species is configured such that each binding section of the species will specifically hybridize to only one other species under a hybridization condition, ensuring an ordered and specific assembly of the species. Because of the unique complementarity between the species, the species can self-assemble to form a specific desired polynucleotide structure (e.g., having a defined width and/or length). In some embodiments, the self-assembly of the species is under an isothermal condition. In some embodiments, the self-assembly of the species is at room temperature. In some embodiments, a species is configured to hybridize with one of the other species in the polynucleotide structure. For example, as shown in FIG. 2, species 10 is configured such that it is hybridized with only species 20, but none of the other species in the polynucleotide structure (although in some embodiments, where it is a linked structure, it could hybridize to species 70 for a tube formation. In some embodiments, a species is configured to hybridize with at least two of the other species in the polynucleotide structure. For example, as shown in FIG. 2, species 20 is hybridized with species 10, 40, 30 and 60; species 30 is hybridized with species 20 and 70; and species 40 is hybridized with species 20 and 50.

A number of criteria can be used to design the species to achieve the desired properties. These include, for example and without limitation, hybridization kinetics; secondary structure such as including hairpins, self-dimers, and cross-dimers; and stability. The composition of the species is not limited to any particular sequences or number of nucleotides, and is designed based on the particular hybridization function. A species can contain deoxyribonucleotides, ribonucleotides, and their analogs.

Species can be synthesized using standard methods, including commercially available nucleic acid synthesizers or obtained from commercial sources such as Agilent Technologies (Santa Clara, Calif.). In some embodiments, the species can be a single stranded DNA. In some embodiments, the species can be a single stranded RNA. In some embodiments, the species can be a single stranded RNA/DNA hybrid. In some embodiments, nucleotides in the species can be modified. The modification can be used, for example, to increase the stability of the species, such as enhance the nuclease resistance and/or thermodynamic stability of the species; as well as to increase the hybridization affinities and/or pairing stability between the species. Non-limiting examples of modification include, substitution of oxygen atoms by sulfur at various locations in the species to make analogs such as DNA phosphorothioates, 4'-thio RNA, 2'-O-[2-(methoxy)ethyl]-2-thiothymidine ($m^5s^2$Umoe) analog.

Standard methods known in the art can be used to detect the resulting polynucleotide structures, such as nucleic acid ribbons and tubes. For example, AFM images of the polynucleotide structures can be obtained using a multimode scanning probe microscope (Veeco Instruments Inc.), equipped with a Q-Control module for analog AFM systems (Atomic Force F&E GmbH).

Binding Section

The term "binding section" as described herein refers to a portion of a species that is configured to hybridize to a complementary nucleic acid sequence of another species in the polynucleotide structure. The two species that have complementary nucleic acid sequences can be in the same column or in a different column. In some embodiments, a species has at least one, two, three, or four binding sections. In some embodiments, a species has at least one binding section. A binding section of a species is configured such that it specifically hybridizes to another species under a hybridization condition. In some embodiments, the binding section of a species is configured such that it specifically hybridizes to only one other species under a hybridization condition.

In some embodiments, each species in the polynucleotide structure has at least one binding section to allow the species to be hybridized to one or more species in the same column or in a different column. In some embodiments, the first species comprises a first binding section. In some embodiments, the second species comprises a second binding section, a third binding section, a first linkage region, a fourth binding section, and a fifth binding section; where the third species comprises: an sixth binding section, a second linkage region and a seventh binding section; where the fourth single stranded species comprises: a eighth binding section and a ninth binding section; where the fifth species comprises: a tenth binding section and an eleventh binding section; and where the sixth species comprises: a twelfth binding section, a thirteenth binding section, a third linkage region, a fourteenth binding section, and a fifteenth binding section. In some embodiments, the first binding section of the first species binds to the second binding section of the second species. In some embodiments, the third binding section of the second species binds to the eighth binding section of the fourth species. In some embodiments, the fourth binding section of the second species binds to the twelfth binding section of the sixth species. In some embodiments, the fifth binding section of the second species binds to the sixth binding section of the third species. In some embodiments, the seventh binding section of the third species binds to the sixteenth binding section of the seven species. In some embodiments, the ninth binding section of the fourth species binds to the tenth binding section of the fifth species. In some embodiments, the eleventh binding section of the fifth species binds to the thirteenth binding section of the sixth species. In some embodiments, the fourteenth binding section of the sixth species binds to the eighteenth binding section of the eighth species. In some embodiments, the fifteenth binding section of the sixth species binds to the seventeenth binding section of the seventh species. In some embodiments, the eighteenth binding section of the eighth species binds to the twentieth binding section of the seventh species.

Linkage Region

As described herein, the term "linkage region" refers to a portion of the species that is not hybridized to any of the other species in the polynucleotide structure. In some embodiments, this is merely a phosphate backbone. In some embodiments, this allows for the "U-like" structure depicted in FIG. 1A. As discussed above, the species can have at least one, two, or three linkage regions. The linkage region can be of various lengths. In some embodiments, the linkage region is 0 nucleotides in length. In some embodiments, the linage region is between two binding sections of a species. In some embodiments, the species includes a linkage region. In some embodiments, the species does not include a linkage region. The term "linked sections," "linked structure", and "U-structure" are used interchangeably herein and denote a section that includes a linkage region.

In some embodiments, the sequence of the species is configured to control the length of the polynucleotide structures. As such, in some embodiments, as one progresses down a row, from a species in a first column to a species in a second column, in the same row, the sequences of the species will differ sufficiently so as to allow selective and ordered hybridization as new columns are added (and the length is increased). In some embodiments, at least two species in a polynucleotide structure has different sequences.

Interaction Between the Species

As discussed above, a species in the polynucleotide structure described herein can interact with at least one of the other species in the polynucleotide structure. The two species that interact with each other can be in the same column or in different columns. The types of interaction between the species are not limited in any way. In some embodiments, a species interact with at least one other species through hybridization (i.e., through complementary sequences). In some embodiments, a species interacts with at least one other species through crosslinking. In some embodiments, a species interact with at least one other species through a covalent bond, for example, a disulfide bond.

Optional Chemical or Enzymatic Treatment for Covalent Linking/Crosslinking

The polynucleotide structure described herein can be chemically or enzymatically modified, for example, to improve the stability of the polynucleotide structure.

In some embodiments, at least one of the species in the polynucleotide structure is ligated to itself. In some embodiments, none of the species is covalently linked to any of the other species in the polynucleotide structure. In some embodiments, the polynucleotide structure comprises more than one inter-locked single stranded nucleotide rings. In some embodiments, at least one of the first, the second, the third, the fourth, the fifth, and the sixth species is ligated to itself.

Methods of ligation of single-stranded polynucleotides are known to those of skill in the art and are described, for example, in Sambrook et al. (2001) which is incorporated herein by reference. Exemplary methods include using T4 RNA ligase 1 which catalyzes ligation of a 5' phosphoryl-terminated nucleic acid donor to a 3' hydroxyl-terminated nucleic acid acceptor through the formation of a 3'→5' phosphodiester bond; a thermostable RNA ligase 1 from a *Thermus Scotoductus* bacteriophage TS2126 (Blondal et al., Nucleic Acids Res. 33(1):135-143 (2005)); ThermoPhage™ single-stranded DNA ligase (Matis, Iceland) which can effectively ligate both single-stranded DNA and RNA; and Taq DNA Ligase which catalyzes the formation of a phosphodiester bond between juxtaposed 5' phosphate and 3' hydroxyl termini of two adjacent oligonucleotides which are hybridized to a complementary target DNA. In some embodiments, linking can be achieved by chemical ligation and/or enzymatic ligation.

The species in a polynucleotide structure can also be covalently crosslinked to preserve or enhance the physical connection between the species, and thus to stabilize the polynucleotide structure. In some embodiments, at least one of the species is covalently crosslinked to at least one of the other species in the polynucleotide structure. In some embodiments, at least one of the species is covalently crosslinked to at least two of the other species in the polynucleotide structure. In some embodiments, at least one of the species is covalently crosslinked to four of the other species in the polynucleotide structure. In some embodiments, at least one of the first, the second, the third, the fourth, the fifth, and the sixth species is crosslinked to at least one of the other species. For example, the first species can be crosslinked to the second species; the second species can be crosslinked to the first, the fourth, the third, and/or the sixth species; the third species can be crosslinked to the second and/or the seventh species; the fourth species can be crosslinked to the second and/or the fifth species; the fifth species can be crosslinked to the fourth and/or the sixth species; the sixth species can be crosslinked to the second, the fifth, the seventh, and/or the eighth species; the second species can be crosslinked to the third and/or the sixth species; and/or the eighth species can be crosslinked to the sixth species.

Crosslinking can be accomplished in any suitable way and by any suitable means appreciated by persons skilled in the art. For example, a crosslinking moiety can be used to crosslink the species. In some embodiments, the species can comprise a crosslinking moiety. For example, the crosslinking moiety can be directly incorporated into the species at the time of synthesis through the use of appropriately modified nucleoside or nucleotide derivatives. The crosslinking moiety can also be incorporated into a species enzymatically by ligating an appropriately modified oligonucleotide which contains a crosslinking moiety. In some embodiments, the crosslinking agent can be introduced into the species-species duplex after hybridization, for example using soluble derivatives of the crosslinking agent followed by photochemical or chemical activation.

The crosslinking moiety can be any chemical moiety which is capable of forming a covalent crosslink between species. Crosslinker moieties are known to those skilled in the art. For example, U.S. Pat. Nos. 4,599,303 and 4,826,967 describe crosslinking compounds based on furocoumarin; U.S. Pat. No. 5,082,934 describes a photoactivatible nucleoside analogue comprising a coumarin moiety linked through its phenyl ring to a ribose or deoxyribose sugar moiety without an intervening base moiety; and U.S. Pat. No. 6,005,093 describes non-nucleosidic, stable, photoactive compounds that can be used as photo-crosslinking reagents in nucleic acid hybridization assays. These references are incorporated herein by reference in their entirety for the teaching of crosslinking moieties. Examples of precursors to the crosslinking moiety include, but are not limited to coumarin, e.g., 7-hydroxycoumarin, 6,7-dihydroxycoumarin, 6-alkoxy-7-hydroxycoumarin, a haloalkyl coumarin; furocoumarin, e.g., a haloalkyl furocoumarin; psoralen, e.g., 8-methoxypsoralen, 5-methoxypsoralen, 4,5',8-trimethylpsoralen, 4'-hydroxymethyl-4,5',8-trimethylpsoralen, and 4'-aminomethyl-4,5',8-trimethylpsoralen; benzodipyrone, e.g., haloalkyl benzodipyrone; or a derivative thereof.

A variety of agents can be used for covalent crosslinking of polynucleotides, including alkylating agents like nitrogen mustard derivatives, and ultraviolet light-activated agents like derivatives of psoralen. The nature of the formation of the covalent bond comprising the crosslink will depend upon the crosslinking moiety chosen. For example, the activation of the covalent bond can occur photochemically, chemically or spontaneously.

Method of Making Nucleic Acid Ribbons and Tubes

Figure 3:
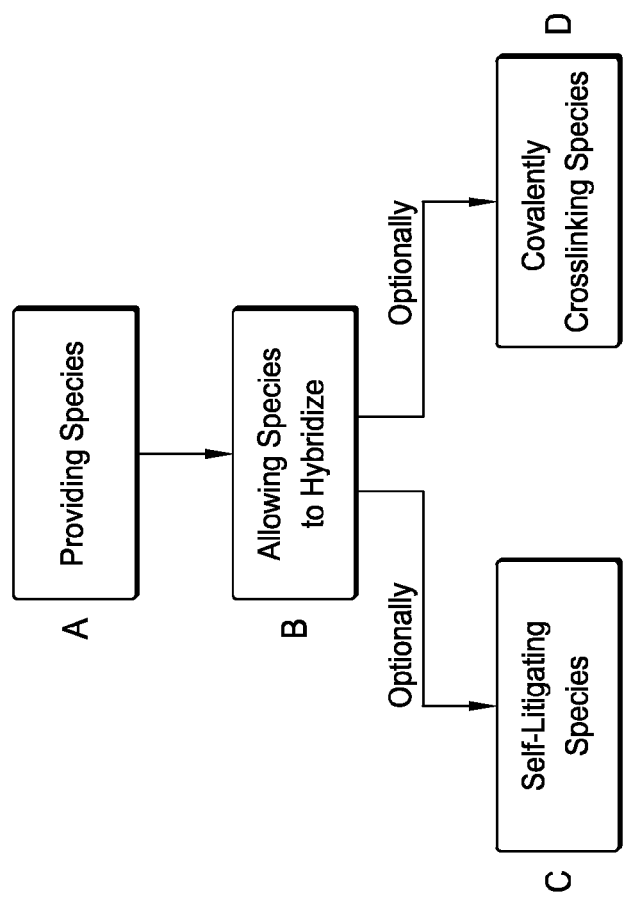
FIG. 3 is a flow chart depicting some embodiments of making a nucleic acid ribbon from a collection of species.

Some embodiments described herein provide a method of making a polynucleotide structure, for example, a nucleic acid ribbon or a nucleic acid tube. An exemplary embodiment of the method is illustrated in FIG. 3: various species are provided (e.g., bought, obtained, aliquoted, made, etc.), and the species are then maintained under conditions to allow hybridization and self-assembly to form the polynucleotide structure.

Figure 4:
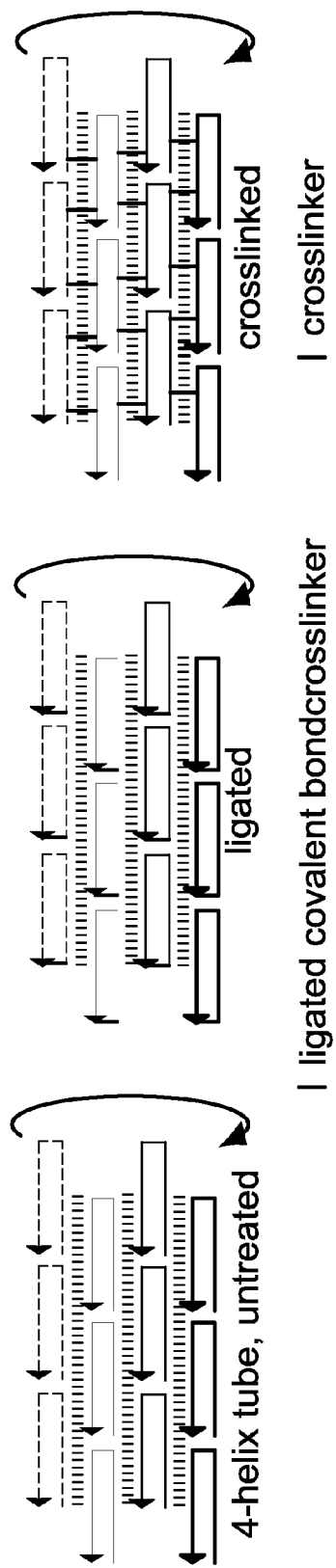
FIGS. 4A-4C depict some embodiments of 4-helix nucleic acid tube made from a collection of species.

In some embodiments, after self-assembly, the species can be self-ligated or covalently crosslinked to enhance the stability of the polynucleotide structure. A schematic depiction of an exemplary embodiment of an untreated 4-helix tube and the 4-helix tube with ligated covalent bond or crosslinker is shown in FIG. 4A-C.

In some embodiments, the method comprises providing a first species 10, a second species 20, a third species 30, a fourth species 40, a fifth species 50, and a sixth species 60, wherein the sequence of the first species 10 is different from the sequence of the fourth species 40; and maintaining the first, the second, the third, the fourth, the fifth, and the sixth species in conditions that allow the first, second, and third species to hybridize to form a first column (e.g., Column 1 in FIG. 1), allow the fourth, fifth, and sixth species to hybridize to form a second column (e.g., Column 2 in FIG. 1), and allow the first column to hybridize to the second column to provide a length to the polynucleotide structure. In some embodiments, assembly occurs via formation of at least part of a column (e.g., first and second species), and then either more of the column (e.g., third species) or the formation of a row (e.g., fourth species).

In some embodiments, the sequence of each species in a row will be different. In some embodiments, the sequence of each adjacent species in a row will be different. In some embodiments, the sequence of each species in a column is different. In some embodiments, the sequence of each adjacent species in a column will be different. In some embodiments, the difference is adequate to allow the ordered and unique assembly of the species into a desired structure. In some embodiments, the sequence of the second species is different from the sequence of the fifth species. In some embodiments, the sequence the third species is different from the sequence of the sixth species. In some embodiments, the sequence the first species is different from the sequence of the second species and the third species. In some embodiments, the sequence of the second species is different from the sequence of the first species and the third species. In some embodiments, the sequence of the third species is different from the sequence of the first species and the third second species.

In some embodiments, the species are maintained in conditions that allow the first species to be hybridized to the second species, and the second species to be hybridized to the third species. In some embodiments, the species are maintained in conditions that allow the third species to be hybridized to the second species, and the fifth species to be hybridized to the fourth and sixth species. In some embodiments, the species are maintained in conditions that allow the second species to be hybridized to the fourth and/or sixth species. In some embodiments, the species are maintained in conditions that allow the third species to be hybridized to the sixth species.

In some embodiments, the method further comprises ligating at least one of the species. In some embodiments, the method further comprises crosslinking at least two of the species. In some embodiments, the first column comprises a top and a bottom, and the method further comprises hybridizing the top and the bottom of the first column to form a tube of the polynucleotide.

Flow-Based Polymerization

Figure 5:
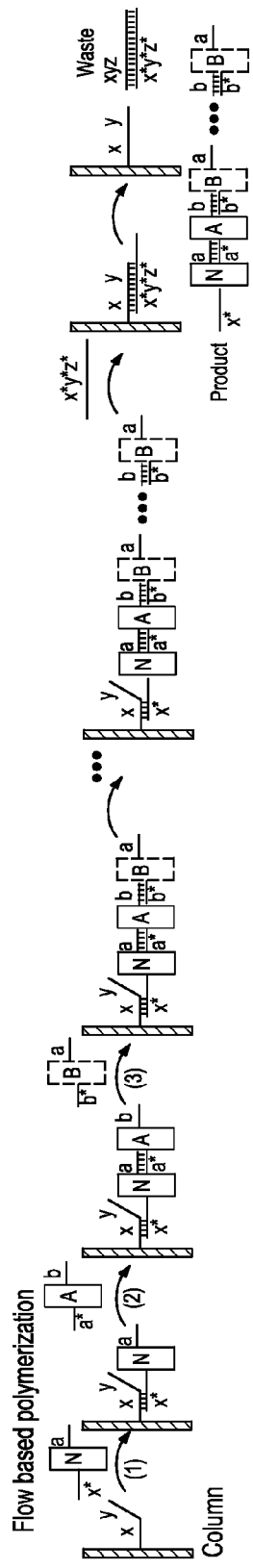
FIG. 5 depicts some embodiments of making a polynucleotide structure from a collection of species using a flow-based polymerization system.

The polynucleotide structure described herein can also be synthesized using a flow-based polymerization system. An exemplary embodiment is illustrated in FIG. 5. As shown in FIG. 5, in step 1, the first layer of tiles, depicted as a rectangle labeled with N is attached to a solid support (labeled as column) by hybridizing to a single stranded nucleic acid immobilized on the solid support, where the hybridization is through the interaction between sticky ends x and x*. In step 2, the second layer, consisting of (or consisting essentially of or comprising) tiles of type A are attached to the first layer consisting (or consisting essentially of or comprising) of tiles of type N. In step 3, the third layer, consisting (or consisting essentially of or comprising) of tiles of type B, are attached. After n steps, a polynucleotide structure of length n is synthesized. Optionally, the polynucleotide structure of length n can be released from the solid support by introducing strand x-y-z to displace strand x*-y*-z* from the solid support, regenerating the attachment site. Such flow-based polymerization approach only requires 3 m different SST species for assembling an m-helix polynucleotide of length n.

Figure 6:
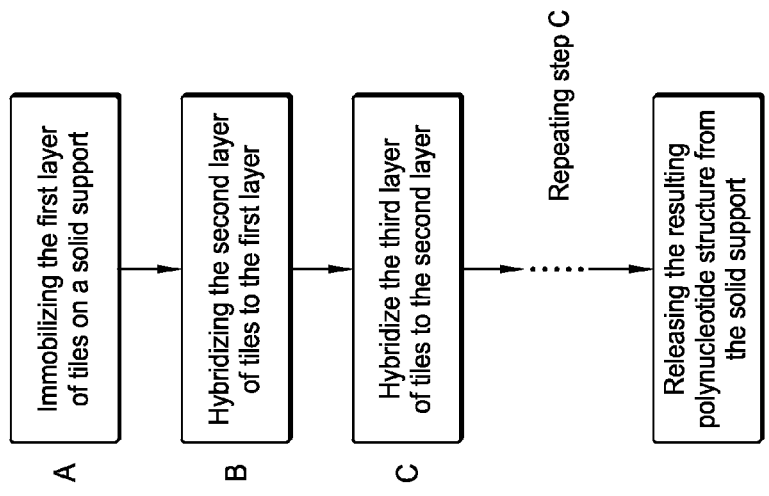
FIG. 6 is a flow chart depicting some embodiments of making a polynucleotide structure from a collection of species using a flow-based polymerization system.

In some embodiments, the method for making a polynucleotide structure comprises: assembling a first, a second and a third species to form a first column; assembling a fourth, a fifth and a six species to form a second column; immobilizing a nucleic acid fragment on a solid support; hybridizing the first column with the nucleic acid fragment; and hybridizing the second column with the first column, wherein the sequence of the first species is different from the sequence from the fourth species. In some embodiments, the method further provides releasing the first column from the solid support. In some embodiments, the assembly and the hybridization steps are under isothermal conditions. In some embodiments, the assembly and the hybridization steps are at room temperature. In some embodiments, the assembly and the hybridization steps are under thermal cycling. As used herein, the solid support can be any solid or semi-solid substrate to which nucleic acid molecules can be immobilized. In some embodiments, a solid support is a solid substrate. In some embodiments, a solid support can comprises a bead or other microparticle. In other embodiments, a solid support comprises a flow chamber or flow cell. In some embodiments, assembly is on a species by species basis, instead of a column by column basis. An embodiment of the method is described in the flow chart shown in FIG. 6.

Flow-Based Doubling

Figure 7:
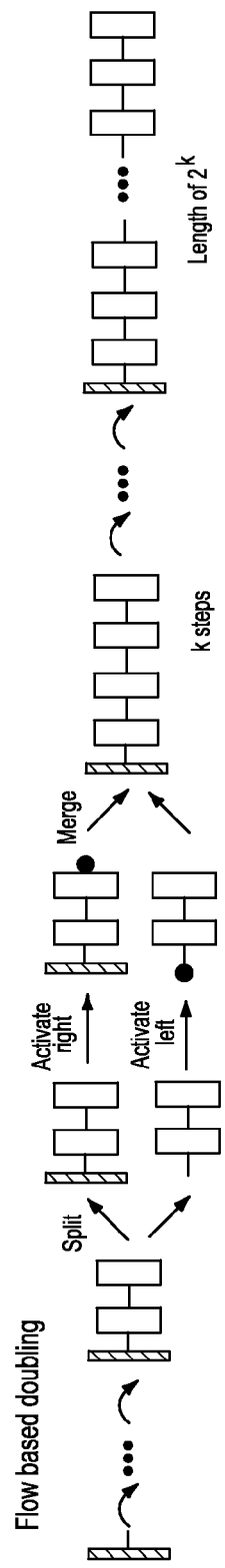
FIG. 7 depicts some embodiments of making a polynucleotide structure from a collection of species using a flow-based doubling system.

In some embodiments, the polynucleotide structure described herein, and other structures, can be synthesized using a flow-based doubling system. An exemplary embodiment is illustrated in FIG. 7, which describes a method that takes only about log k steps by doubling the length of the polynucleotide structure in each step. In some embodiments, this is achieved by displacing half of the polynucleotide structures from the column, and then specifically activating the 5' end of the polynucleotide structures that are immobilized on the solid support and activate the 3' end of the polynucleotide structures that are displaced from the solid support. When the two pools of polynucleotide structures are merged, the polynucleotide structures can be linked to double the length of the polynucleotide structures immobilized to the column. Accordingly, in log k steps, a polynucleotide structure of length 2 k can be synthesized.

Figure 8:
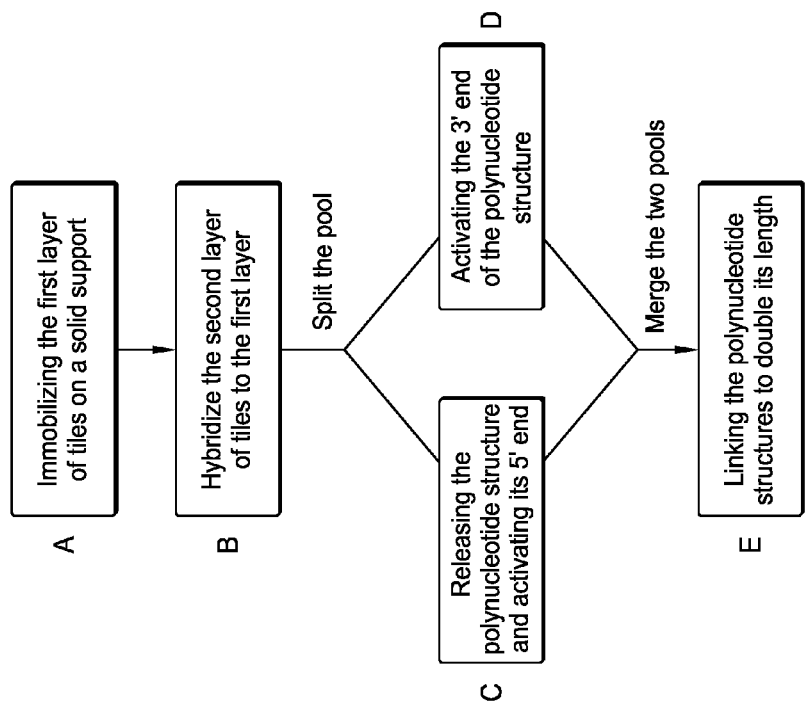
FIG. 8 is a flow chart depicting some embodiments of making a polynucleotide structure from a collection of species using a flow-based doubling system.

In some embodiments, the method comprises: (a) assembling a first, a second and a third species to form a plurality of first columns; (b) assembling a fourth, a fifth and a six species to form a plurality of second columns; (c) immobilizing the first columns on a solid support; (d) hybridizing the second columns with the first columns to form a plurality of first polynucleotide units; and (e) ligating at least two of the first polynucleotide units to form a second polynucleotide units. An embodiment of the method is described in the flow chart shown in FIG. 8.

Method of Building 2D/3D Objects Using Nucleic Acid Ribbons and Tubes

In some embodiments, the nucleic acid ribbons and/or tubes described in the present application can be used to build 2D/3D objects, for example, large-scale 2D/3D objects 1-100 μm in diameter. Rigid molecular rods (for example, nucleic acid ribbons or tubes) with precisely controlled diameters, lengths, and programmable sticky ends at both ends of the rods can be synthesized according to the methods described herein. These molecule rods can be used as basic building blocks for constructing large 2D/3D shapes of prescribed geometry.

In some embodiments, the molecular rods can be assembled into the tetrahedron where the vertices are 3D objects produced using 3D DNA origami technique. "DNA origami" refers to the technique of using multiple oligonucleotides (helper strands) to fold a longer polynucleotide at desired locations in the scaffold, which is the longer sequence (see, e.g., Rothemund 2006, which is incorporated by reference in its entirety). For example, a circular, single stranded DNA can be folded into a variety of shapes by selection of short, single-stranded "helper strands" that hybridize to the single stranded DNA at predetermined locations. In particular the helper strand can have at least two regions that each hybridizes to different locations of the single stranded DNA. Thus, the helper strands can, by simultaneously hybridizing to two or more distant regions of the single stranded DNA, fold the single stranded DNA. DNA origami can therefore be used to controllably position different nucleotides of a large DNA complex relative to one another in 2D or 3D space. "DNA origami" can also be used with other nucleic acids (e.g., RNA) and nucleic acid analogs (e.g., peptide nucleic acids, PNA). An exemplary embodiment of the method for constructing a tetrahedron using DNA origami technique is illustrated in FIG. 9A.

Figure 9B:
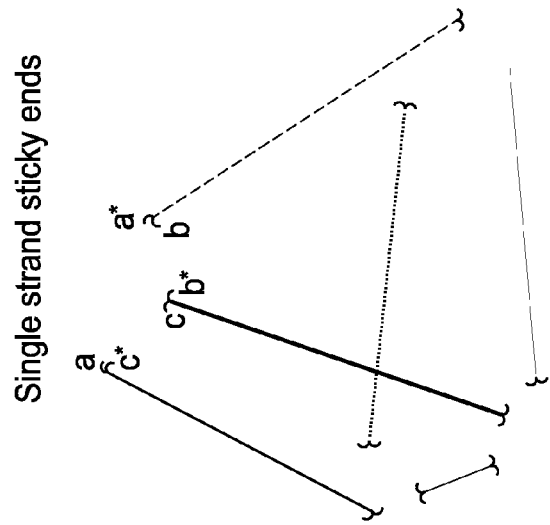
FIGS. 9A and 9B depict some embodiments of making a nucleic acid tetrahedron from a collection of nucleic acid ribbons and/or nucleic acid tubes.
Figure 9A:
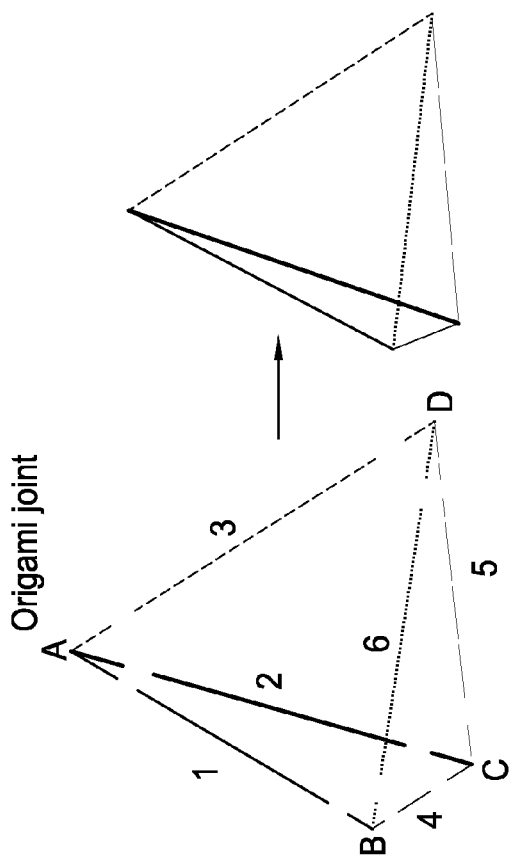

Another exemplary embodiment of the method for constructing a tetrahedron is illustrated in FIG. 9B. In this approach, a polynucleotide structure, such as a nucleic acid ribbon or nucleic acid tube described herein, is considered to be a molecular rod. In some embodiments, each molecular rod is configured to carry sticky ends that are programmed to be complementary to the sticky ends of other molecular rods in a suitable fashion such that by matching the sticky ends, these molecular rods can be assembled into the tetrahedron. As shown in FIG. 9B, each of the molecular rod comprise two single-stranded sticky ends at either end so that it can hybridize with four of the other five molecular rods to form the tetrahedron.

The assembled 2D/3D objects can be analyzed by standard methods known by one of skill in the art. For example, the 2D/3D objects can be imaged with transmission electron microscopy (TEM). As the objects reaches desired large size (e.g., 1-100 μm in diameter), they can be stained with fluorescent dyes and imaged with fluorescent microscope.

Applications for Various Embodiments

Some embodiments of the polynucleotide structures described in the present application, for example, the nucleic acid ribbons, the nucleic acid tubes, or the larger 2D/3D nucleic acid objects, have a wide variety of uses.

Nanotechnology has made remarkable progress in manufacturing individual molecular devices (e.g. metallic particles, quantum dots, carbon nanotubes) with great precision. However, it remains a major challenge to organize such entities into complex and functional systems. Thanks to the rich attachment chemistry of nucleic acids, synthetic polynucleotide structures, such as the structures disclosed herein, can serve as scaffolds for organizing functional inorganic particles and devices with nanometer precision, e.g. gold nanoparticles, quantum dots, and carbon nanotubes. Such templating capabilities coupled with the construction of increasing complex DNA structures, such as those described herein, allows numerous applications in electronics, plasmonics, and quantum computing. For example, carbon nanotubes can be organized into functional molecular electronics systems; tunable geometric organization of gold nanoparticles can result in functional molecular electronics circuits and novel plasmonics circuits; organization of magnetic particles can result in the construction of nano-inductors or memory devices; organization of quantum dots can allow the construction of novel quantum computers.

In some embodiments, the polynucleotide structures described herein can also be metalized for electronics. DNA tubes have been metalized into nanowires. Controlled metalization of the polynucleotide nano-tubes with programmable circumferences can result in nano-wires with controlled diameters and hence controlled electronic properties. And novel molecular electronic components and circuits can be fabricated through controlled metalization of the strut based polynucleotide structures described herein.

In addition, the polynucleotide structures described herein can be used for templating biological molecules for biomedical research. Various strategies have been demonstrated for templating protein molecules on DNA lattices. Organization of proteins into prescribed geometric patterns with programmable nanometer precision has been suggested to study the cooperative behavior of biological motor proteins. The nucleic acid nano-ribbons and nano-tubes described herein can be aligned into lattices via controlled surface deposition on microfabricated 2D surfaces, and be functionalized with relevant molecular cues (e.g. growth factors covalently linked to DNA strands) to serve as synthetic microenvironment to guide/study cell development, differentiation, and motion, e.g., neural cell polarization. In addition, the large 3D polynucleotide objects disclosed herein (i.e., 3D DNA nanotube matrices) can serve as artificial scaffolds for 3D cell culture and study.

EXAMPLE

The following examples, including the experiments conducted and results achieved are provided for illustrative purposes only and are not to be construed as limiting upon the present application.

Example 1

Synthesizing a 3-Helix DNA Ribbon with Predetermined Length

This example illustrates a method for synthesizing a 3-helix DNA ribbon with a predetermined length of k columns using 4 k distinct single-stranded DNA (ssDNA) species.

The 4 k distinct ssDNA species are commercially synthesized and purified in two batches using denaturing PAGE. One batch is for the 2 k U species that all have identical lengths of 42 bases, and the other batch is for the 2 k L species that all have identical lengths of 21 bases. All ssDNA are mixed in TAE/$Mg^{2+}$ buffer (20 mM Tris, pH 7.6, 2 mM EDTA, 12.5 mM $MgCl_2$) and incubated in a water bath from 90° C. to 23° C. over a period of 24 hours. The self-assembled structures are characterized using atomic force microscope. The schematic illustration of the resulting 3-helix DNA ribbon is shown in FIG. 1C.

Example 2

Synthesizing a 4-Helix DNA Tube with Predetermined Length

This example illustrates a method for synthesizing a 4-helix DNA tube with a predetermined length of k columns using 4 k distinct single-stranded DNA (ssDNA) species.

The 4 k distinct ssDNA species that all have identical length of 42 bases are commercially synthesized and purified in two batches using denaturing PAGE. All ssDNA are mixed in TAE/$Mg^{2+}$ buffer (20 mM Tris, pH 7.6, 2 mM EDTA, 12.5 mM $MgCl_2$) and incubated in a water bath from 90° C. to 23° C. over a period of 24 hours. The self-assembled structures are characterized using atomic force microscope. The schematic illustration of the resulting 4-helix DNA tube is shown in FIG. 4A.

In order to improve the stability of the 4-helix DNA tube, each of the ssDNA species in the DNA tube are ligated to itself using T4 RNA ligase (FIG. 4B. In this case, although each ssDNA species is not covalently linked with its neighbors, due to the helical nature of DNA, each ssDNA species is actually wrapped around its two vertical neighbors, and hence the 4-helix tube really behaves as one big molecule composed of inter-locked SST rings, and such rings cannot be separated from each other without breaking a covalent bond.

Alternatively, each of the ssDNA species are covalently cross-linked to its neighbor ssDNA species using for example psoralen or thiol-ene (FIG. 4C.

Although the present application has been described in detail above, it will be understood by one of ordinary skill in the art that various modifications can be made without departing from the spirit of the invention. Accordingly, the present application is limited only by the following claims. All cited patents, patent applications and publications referred to in this application are herein incorporated by reference in their entirety.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

As will be appreciated by one of skill in the art, while the present specification may simply use one of the terms "comprise," "consists," or "consists essentially of," this is simply a shorthand way of describing all three possibilities, unless otherwise specified or unless the term is used in the claim (in which case the terms will have their normally accepted meanings under claim interpretation). Thus, as the terms are used above, they designate all three possibilities, unless explicitly noted otherwise.

What is claimed is:

1. A method of making a polynucleotide structure, comprising:
providing a first species, a second species, a third species, a fourth species, a fifth species, and a sixth species, wherein the sequence of the first species is different from the sequence of the fourth species;
maintaining the first, the second, the third, the fourth, the fifth, and the sixth species in conditions that 1) allow the first, second, and third species to hybridize to form a first column comprising at least a portion of each of the first, second, and third species, wherein the first column comprises at least two double-stranded polynucleotide helices, 2) allow the fourth, fifth, and sixth species to hybridize to form a second column comprising at least a portion of each of the fourth, fifth, and sixth species, wherein the second column comprises at least two double-stranded polynucleotide helices, and 3) allow the first column to hybridize to the second column to provide a polynucleotide structure of a defined length.

2. The method of claim 1, wherein the conditions allows the first species to be hybridized to the second species and the second species to be hybridized to the third species.

3. The method of claim 1, further comprising providing a seventh species and an eighth species, and maintaining the seventh species and the eighth species in conditions that the seventh species hybridizes to the third species and the eighth species to be hybridizes to the sixth species.

4. The method of claim 3, further comprising hybridizing the first and the seventh species to form a tube of the polynucleotide, wherein the tube comprises at least a top of the first column positioned adjacent to a bottom of the first column.

5. The method of claim 1, further comprising covalently bonding at least two of the first, the second, the third, the fourth, the fifth, and the sixth species.

6. The method of claim 1, further comprising ligating at least one of the first, the second, the third, the fourth, the fifth, and the sixth species to itself.

7. A polynucleotide structure comprising:
a first species;
a second species;
a third species;
a fourth species;
a fifth species; and
a sixth species,
wherein the first, the second, and the third species are hybridized to form a first column that comprises at least a portion of each of the first, second and third species, wherein the first column comprises at least two double-stranded polynucleotide helices, wherein the fourth, the fifth, and the sixth species are hybridized to form a second column that comprises at least a portion of each of the fourth, fifth, and sixth species, wherein the second column comprises at least two double-stranded polynucleotide helices, wherein the first column is hybridized to the second column, providing a length to the polynucleotide structure, and wherein the sequence of the first species is different from the sequence of the fourth species, and wherein the first and fourth species comprise a first row.

8. The polynucleotide of claim 7, wherein the sequence of the second species is different from the sequence of the fifth species.

9. The polynucleotide of claim 8, wherein the sequence the third species is different from the sequence of the sixth species.

10. The polynucleotide of claim 9, wherein the sequence of the first species is different from the sequence of the second species and the third species.

11. The polynucleotide of claim 10, wherein the sequence of the second species is different from the sequence of the first species and the third species.

12. The polynucleotide of claim 7, wherein the sequence of the third species is different from the sequence of the first species and the second species.

13. The polynucleotide of claim 8, wherein the first species is hybridized to the second species, and wherein the second species is hybridized to the third species.

14. The polynucleotide of claim 13, wherein the fifth species is hybridized to the sixth species.

15. The polynucleotide of claim 7, further comprising:
a seventh species; and
an eighth species, wherein the seventh species forms a part of the first column, and wherein the eighth species forms a part of the second column.

16. The polynucleotide of claim 15, wherein the seventh species is hybridized to the third species, and wherein the eighth species is hybridized to the sixth species.

17. The polynucleotide of claim 16, wherein the first and the seventh species are linear.

18. The polynucleotide of claim 16, wherein the second and the third species are U-shaped.

19. The polynucleotide of claim 18, wherein the first and the seventh species are linear.

20. The polynucleotide of claim 19, wherein the first and the seventh species are each 21 nucleotides in length.

21. The polynucleotide of claim 20, wherein the second and the third species are units of 42 nucleotides in length.

22. The polynucleotide of claim 21, wherein the second and the third species are each 42 or 84 nucleotides in length.

23. The polynucleotide of claim 22, wherein the polynucleotide is 2 to one million columns in length.

24. The polynucleotide of claim 19, wherein the polynucleotide is 2 to 1,000 columns in length.

25. The polynucleotide of claim 19, wherein there is at least one covalent bond between at least two of the species.

26. The polynucleotide of claim 25, wherein there is at least one covalent bond between the first species and the seventh species.

27. The polynucleotide of claim 26, wherein the covalent bond comprises a disulfide bond.

28. The polynucleotide of claim 15, wherein the first column comprises a top and a bottom, and wherein the top is adjacent to the bottom, so as to form a tube of the polynucleotide.

29. The polynucleotide of claim 28, wherein the top and bottom of the first column interact by hybridization.

30. The polynucleotide of claim 29, wherein the top and bottom of the first column interact by a covalent bond.

31. The polynucleotide of claim 15, wherein the first and the seventh species interact so as to form a tube of the polynucleotide.

32. The polynucleotide of claim 7, wherein there is at least one covalent bond between at least two of the species.

33. The polynucleotide of claim 26, wherein there is at least one covalent bond between the first and second species.

34. The polynucleotide of claim 7, wherein the second and the fifth species comprise a second row, and wherein the third and the sixth species comprise a third row.

35. The polynucleotide of claim 34, wherein the polynucleotide comprises 1 to 100 rows.

* * * * *